(12) United States Patent
Yamazaki et al.

(10) Patent No.: US 9,087,996 B2
(45) Date of Patent: Jul. 21, 2015

(54) FLUORINE-CONTAINING AROMATIC COMPOUND AND PRODUCTION METHOD THEREOF

(71) Applicant: Asahi Glass Company, Limited, Chiyoda-ku, Tokyo (JP)

(72) Inventors: Takashi Yamazaki, Tokyo (JP); Shigeyuki Yamada, Tokyo (JP); Kyoko Yamamoto, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/460,177

(22) Filed: Aug. 14, 2014

(65) Prior Publication Data
US 2014/0357873 A1 Dec. 4, 2014

Related U.S. Application Data

(63) Continuation of application No. PCT/JP2013/053586, filed on Feb. 14, 2013.

(30) Foreign Application Priority Data

Feb. 17, 2012 (JP) ................................. 2012-033157

(51) Int. Cl.
| H01L 51/00 | (2006.01) |
| C07C 43/225 | (2006.01) |
| C09K 11/06 | (2006.01) |
| C07C 35/52 | (2006.01) |
| C07D 333/12 | (2006.01) |
| H05B 33/10 | (2006.01) |
| C07C 17/35 | (2006.01) |
| C07C 41/30 | (2006.01) |
| C07C 29/09 | (2006.01) |

(52) U.S. Cl.
CPC ............ *H01L 51/0055* (2013.01); *C07C 17/35* (2013.01); *C07C 29/09* (2013.01); *C07C 35/52* (2013.01); *C07C 41/30* (2013.01); *C07C 43/225* (2013.01); *C07D 333/12* (2013.01); *C09K 11/06* (2013.01); *H01L 51/0052* (2013.01); *H01L 51/0068* (2013.01); *H05B 33/10* (2013.01); *C07C 2103/24* (2013.01); *C07C 2103/52* (2013.01); *C09K 2211/1007* (2013.01); *C09K 2211/1011* (2013.01); *C09K 2211/1092* (2013.01)

(58) Field of Classification Search
CPC .................................................. H01L 51/0055
USPC ......................................................... 570/142
See application file for complete search history.

(56) References Cited

U.S. PATENT DOCUMENTS

| 2005/0054870 A1 | 3/2005 | Wu et al. |
| 2006/0273311 A1 | 12/2006 | Ohe et al. |
| 2007/0215902 A1 | 9/2007 | Nakagawa |
| 2009/0140241 A1 | 6/2009 | Ohe et al. |

(Continued)

FOREIGN PATENT DOCUMENTS

| CN | 1894185 A | 1/2007 |
| CN | 1950933 A | 4/2007 |
| CN | 101798293 A | 8/2010 |

(Continued)

OTHER PUBLICATIONS

Gundlach et al., "Thin-film transistors based on well-ordered thermally evaporated naphthacene films," Applied Physics Letters, vol. 80, No. 16, Apr. 22, 2002, p. 2925-2927.
International Search Report dated May 21, 2013 issued in Application No. PCT/JP2013/053586.
Sun et al. "Arene Trifluoromethylation: An Effective Strategy to Obtain Air-Stable n-Type Organic Semiconductors with Tunable Optoelectronic and Electron Transfer Properties," The Journal of Physical Chemistry A, Jul. 10, 2012, vol. 116, No. 30, p. 8015-8022, Table 2, Pentacene_6, 13-CF3.

(Continued)

*Primary Examiner* — Taofiq A Solola
(74) *Attorney, Agent, or Firm* — Foley & Lardner LLP

(57) ABSTRACT

A method of manufacturing a fluorine-containing aromatic compound represented by the following formula (2-1) or formula (2-2): $R_1$ is a linear perfluoroalkyl group having a carbon number of 1 to 3; $X_2$ to $X_5$ are a halogen atom or a hydrogen atom; $R_2$ to $R_5$, $L_1$ and $L_2$ are a monovalent hydrocarbon group having a carbon number of 1 to 12, a monovalent aromatic hydrocarbon group, a monovalent hetero aromatic group, a halogen atom, or a hydrogen atom; one or more groups selected from $R_2$ to $R_5$ are a monovalent hydrocarbon group having a carbon number of 1 to 12, a monovalent aromatic hydrocarbon group, or a monovalent heteroaromatic group; and m is an integer of 0 or more, n is an integer of 1 or more, and m+n is an integer of 2 or more and 6 or less.

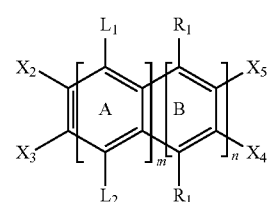

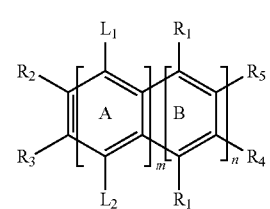

13 Claims, No Drawings

(56) References Cited

U.S. PATENT DOCUMENTS

| | | |
|---|---|---|
| 2009/0230387 A1 | 9/2009 | Ohe et al. |
| 2012/0208989 A1 | 8/2012 | Sun |

FOREIGN PATENT DOCUMENTS

| | | | |
|---|---|---|---|
| EP | 1 737 027 A1 | 12/2006 | |
| JP | S57-075932 A | 5/1982 | |
| JP | A-H02-062832 A | 3/1990 | |
| JP | 2007-013097 A | 1/2007 | |
| WO | WO-2006/019133 A1 | 2/2006 | |
| WO | WO-2011/022678 A1 | 2/2011 | |

OTHER PUBLICATIONS

Meijere, et al., "1,3-Bicyclo[1.1.1]pentanediyl: The Shortest Rigid Linear Connector of Phenylated Photochromic Units and a 1,5-Dimethoxy-9,10-di(phenylethynyl)anthracene Fluorophore," Chem. Euro. J. 2007, vol. 13, pp. 2503-2516.

Singh, et al., "Synthesis and characterization of novel trifluoromethyl-containing alcohols with Ruppert's reagent," Journal of Fluorine Chemistry, vol. 133 (2012), pp. 20-26.

FLUORINE-CONTAINING AROMATIC COMPOUND AND PRODUCTION METHOD THEREOF

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/053586 filed on Feb. 14, 2013, which is based upon and claims the benefit of priority of Japanese Application No. 2012-033157 filed on Feb. 17, 2012, the entire contents of which are hereby incorporated by reference in their entireties.

TECHNICAL FIELD

The present invention relates to a novel fluorine-containing aromatic compound applicable to organic semiconductor materials and a manufacturing method thereof.

BACKGROUND ART

Since an organic semiconductor element using an organic compound as a semiconductor material exhibits easiness in workability as compared with conventional semiconductor elements using inorganic semiconductor materials such as silicon, it has been expected to realize a low-cost device. Moreover, since a semiconductor material of an organic compound is structurally flexible, it has been expected to realize a device such as a flexible display by using the material in combination with a plastic substrate.

As working processes for organic semiconductors, there is known a dry process by vapor deposition and a wet process using an organic solvent, such as coating, printable, or ink jet. Since a conventional organic semiconductor material has a low solubility in organic solvents and thus it is difficult to apply the wet process thereto, the dry process has been widely utilized. On the other hand, the wet process is easy and inexpensive and is a manufacturing process exhibiting a little environmental burden.

An improvement in carrier mobility is required for an organic semiconductor material. As a method for improving the carrier mobility of the organic semiconductor material, an effective method has not yet been established but it is considered to be important to strengthen intermolecular interaction or control arrangement of molecules. For example, since an acene compound that is a condensed polycyclic compound has an expanded conjugate system owing to its planar structure and has a strong intermolecular interaction owing to π stacking, it is attempted to utilize the compound as an organic semiconductor material (Non-Patent Document 1).

An acene compound is a compound having a skeleton in which benzene rings are linearly condensed. The acene compound has a small theoretical band gap as compared with polyacetylene and the like and thus an excellent function as an organic semiconductor material is expected and the function is expectable as the number of rings increases. Moreover, the compound has a possibility of changing conductivity depending on a substituent.

In an acene compound having no substituent on the ring group, solubility in an organic solvent decreases as the number of the rings increases. Therefore, it is difficult to apply the wet process to the acene compound. Also, in the case of applying the wet process, there is very narrow range for selecting solvent and temperature condition.

There is proposed an acene compound having an increased affinity to organic solvents by introducing a substituent such as an alkyl group into the acene skeleton (Patent Document 1). However, a compound having a fluorine-containing alkyl group as a substituent is not investigated.

Patent Document 2 discloses a method for manufacturing an acene compound having a perfluoroalkyl group by a coupling reaction using a heavy metal. As the acene compound, a compound having $nC_8F_{17}-$ groups substituted at 6- and 13-positions of anthracene is disclosed.

PRIOR ART DOCUMENTS

Patent Documents

Patent Document 1: JP-A-2007-13097
Patent Document 2: WO 2011/022678

Non-Patent Documents

Non-Patent Document 1: D. J. Gundlach, S. F. Nelson, T. N. Jachson et al., Appl. Phys. Lett., (2002), 80, 2925.

SUMMARY OF THE INVENTION

Problems that the Invention is to Solve

However, in the method described in Patent Document 2, since a coupling reaction of a halo-substituted acene compound with a perfluoroalkyl iodide in the presence of a heavy metal is applied, synthesis becomes vexatious and complicated and contamination with the heavy metal becomes a problem. In general, since an organic semiconductor material is required to be highly pure, much labor is necessary for ultrahigh purification.

According to the conventional technologies, organic semiconductor materials expectable to exhibit high carrier mobility are mainly obtained by a dry process and such materials have a low solubility in solvents. On the other hand, organic semiconductor materials having a high solubility in solvents, which are obtained by a wet process, have low carrier mobility. Moreover, since the acene compounds obtained by conventional technologies utilize a heavy metal at the time of introducing a substituent, there is a concern that the carrier mobility as organic semiconductors is lowered due to remaining of the heavy metal.

Accordingly, an object of the present invention is to provide a compound applicable to both of a dry process and a wet process and useful as an organic semiconductor material having high carrier mobility.

Specifically, a first object thereof is to provide a compound soluble even in a low polar solvent and expectable to have high carrier mobility resulting from a strong intermolecular interaction. Moreover, a second object thereof is to provide a compound having a little contamination with heavy metals which is one cause of a decrease in carrier mobility.

Means for Solving the Problems

As a result of extensive studies for solving the above problems and achieving the objects, the present inventors have newly found a fluorine-containing aromatic compound having a specific structure, which has a little contamination with heavy metals and is relatively soluble even in a low polar solvent, and a manufacturing method thereof. Thus, they have accomplished the present invention.

That is, the present invention relates to the followings.
<1>
A fluorine-containing aromatic compound selected from a compound represented by the following formula (2-1) and a compound represented by the formula (2-2):

[Chem 1]

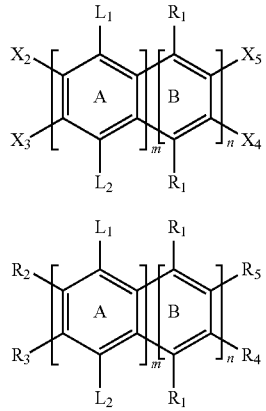

(2-1)

(2-2)

[In the formulae, $R_1$ is a linear perfluoroalkyl group having a carbon number of to 3.

$X_2$ to $X_5$ are a halogen atom or a hydrogen atom and they may be the same or different.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent. $R_2$ to $R_5$ may be the same or different.

m and n are the numbers of repetitions of repeating unit structures A and B represented in parentheses, respectively, m is an integer of 0 or more, n is an integer of 1 or more, and m+n is an integer of 2 or more and 6 or less.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different. In the case where m is 2 or more, a plurality of the $L_1$ groups present in the structure A may be the same or different and a plurality of the $L_2$ groups present in the structure A may be the same or different.

In the case where at least one of m and n is 2 or more, the order of combining the structure A and the structure B may be block or random.

However, when m is 2, n is 1 and the order of the repeating unit structures is A-B-A, the case where $R_1$ is —$CF_3$ and $X_2$ to $X_5$, $L_1$, and $L_2$ are hydrogen atoms is excluded.]
<2>
The fluorine-containing aromatic compound according to the above <i>, in which the compound represented by the formula (2-1) is a compound represented by the following formula (3-1) and the compound represented by the formula (2-2) is a compound represented by the following formula (3-2):

[Chem. 2]

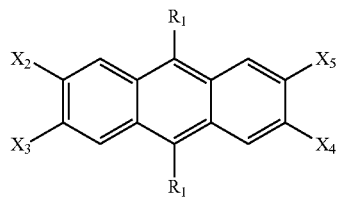

(3-1)

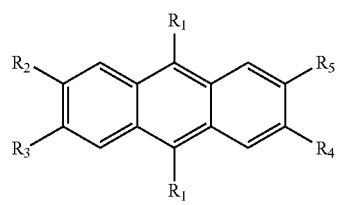

(3-2)

[In the formulae, $X_2$ to $X_5$ and $R_1$ to $R_5$ represent the same meanings as mentioned above. However, the case where $R_1$ is —$CF_3$ and $X_2$ to $X_5$ are hydrogen atoms is excluded.]
<3>
The fluorine-containing aromatic compound according to the above <1>, in which the compound represented by the formula (2-1) is a compound represented by the following formula (4-1) or a compound represented by the following formula (5-1) and the compound represented by the formula (2-2) is a compound represented by the following formula (4-2) or a compound represented by the following formula (5-2):

[Chem 3]

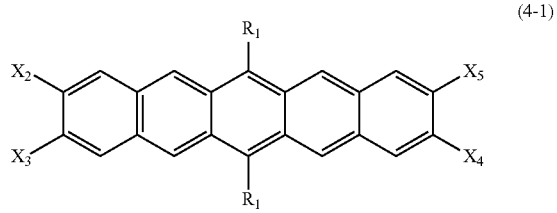

(4-1)

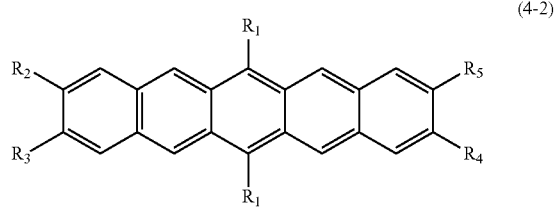

(4-2)

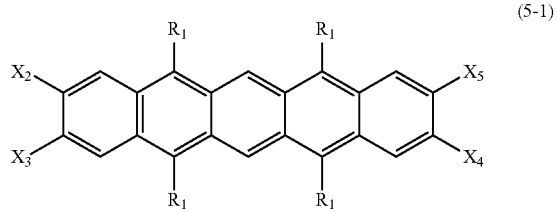

(5-1)

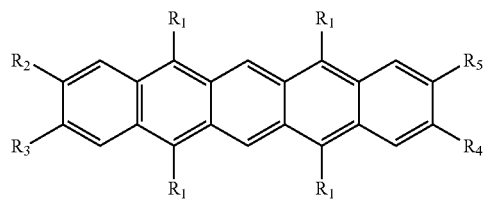
(5-2)
[In the formulae, $X_2$ to $X_5$ and $R_1$ to $R_5$ represent the same meanings as mentioned above.]
<4>
A fluorine-containing aromatic compound selected from compounds represented by the following formulae:
[Chem 4]
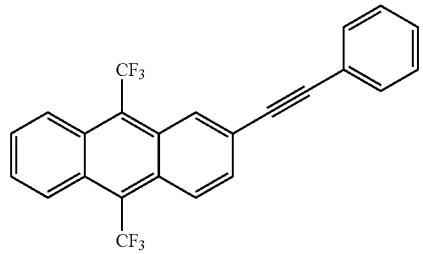
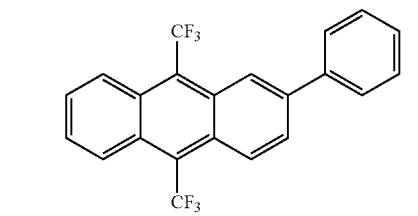
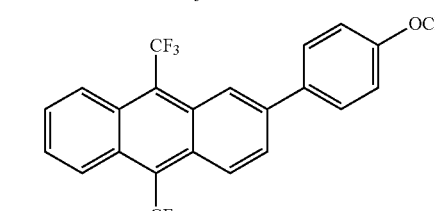
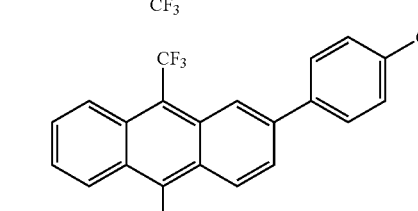
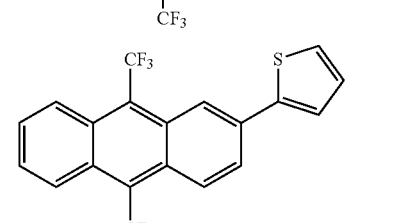
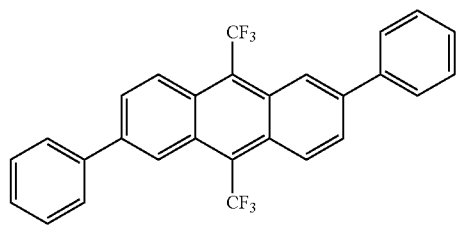
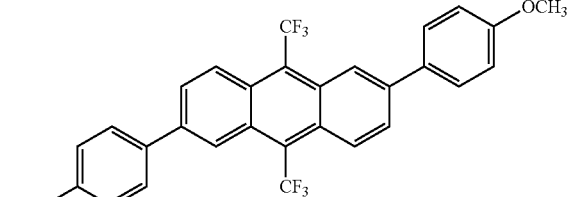
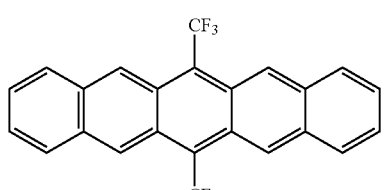
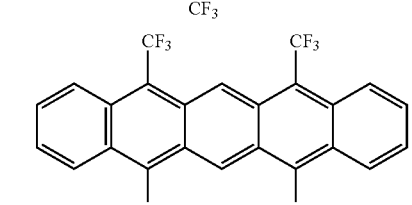
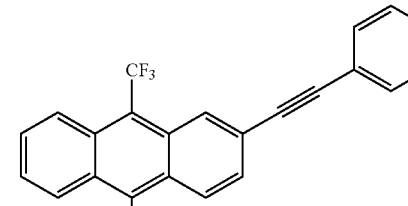
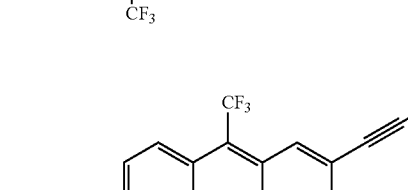
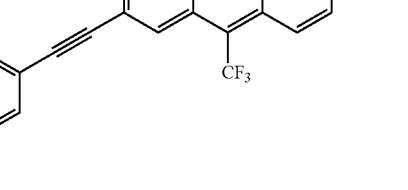

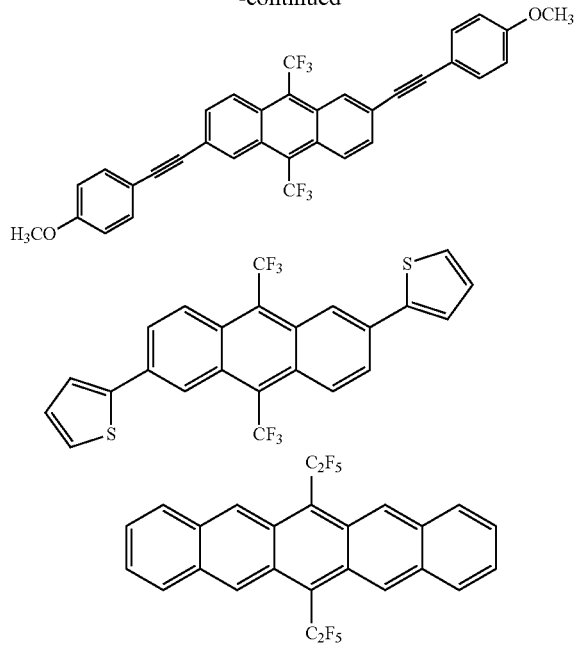

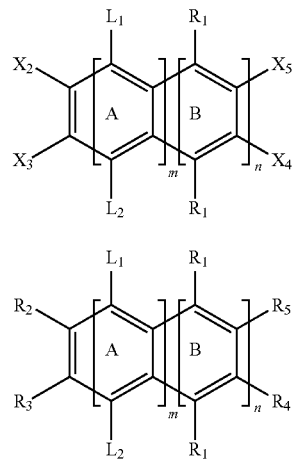

<5>

The fluorine-containing aromatic compound according to any one of the above <1> to <4>, in which the amount of heavy metals in 1 g of the compound is 20 μg or less.

<6>

An organic semiconductor material containing the fluorine-containing aromatic compound described in any one of the above <1> to <5>.

<7>

An organic semiconductor thin film containing the organic semiconductor material described in the above <6>.

<8>

An organic semiconductor thin film containing the organic semiconductor material described in the above <6> and having crystallinity.

<9>

An organic semiconductor element containing a substrate and the organic semiconductor thin film described in the above <7> or <8>.

<10>

A transistor containing a gate electrode, a dielectric layer, a source electrode, a drain electrode, and a semiconductor layer, in which the semiconductor layer is composed of the organic semiconductor thin film described in the above <7> or <8>.

<11>

A method for manufacturing a compound represented by the following formula (2-2), the method including: replacing at least one halogen atom of a compound represented by the following formula (2-1) where at least one of $X_2$ to $X_5$ is a halogen atom by a monovalent hydrocarbon group having a carbon number of 1 to 12 which may have a substituent, a monovalent aromatic hydrocarbon group which may have a substituent, a monovalent heteroaromatic group which may have a substituent:

[Chem 5]

[In the formulae, $R_1$ is a linear perfluoroalkyl group having a carbon number of 1 to 3.

$X_2$ to $X_5$ are a halogen atom or a hydrogen atom and they may be the same or different.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent. $R_2$ to $R_5$ may be the same or different.

m and n are the numbers of repetitions of repeating unit structures A and B represented in parentheses, respectively, m is an integer of 0 or more, n is an integer of 1 or more, and m+n is an integer of 2 or more and 6 or less.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different. In the case where m is 2 or more, a plurality of the $L_1$ groups present in the structure A may be the same or different and a plurality of the $L_2$ groups present in the structure A may be the same or different.

In the case where at least one of m and n is 2 or more, the order of combining the structure A and the structure B may be block or random.

However, when m is 2, n is 1 and the order of the repeating unit structures is A-B-A, the case where $R_1$ is —$CF_3$ and $X_2$ to $X_5$, $L_1$, and $L_2$ are hydrogen atoms is excluded.]

<12>

A compound selected from a compound represented by the following formula (1-1) and a compound represented by the following formula (1-2):

[Chem 6]

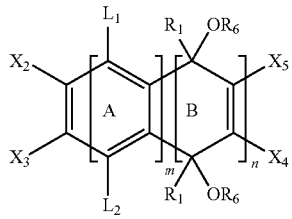
(1-1)

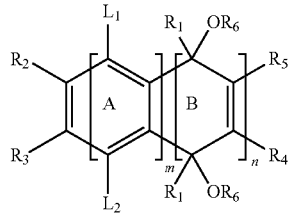
(1-2)

[In the formulae, $R_1$ is a linear perfluoroalkyl group having a carbon number of 1 to 3.

$X_2$ to $X_5$ are a halogen atom or a hydrogen atom and they may be the same or different.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent. $R_2$ to $R_5$ may be the same or different.

$R_6$ is —$Si(CH_3)_3$ or a hydrogen atom.

m and n are the numbers of repetitions of repeating unit structures A and B represented in parentheses, respectively, m is an integer of 0 or more, n is an integer of 1 or more, and m+n is an integer of 2 or more and 6 or less.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different. In the case where m is 2 or more, a plurality of the $L_1$ groups present in the structure A may be the same or different and a plurality of the $L_2$ groups present in the structure A may be the same or different.

In the case where at least one of m and n is 2 or more, the order of combining the structure A and the structure B may be block or random.]

<13>

A method for manufacturing a fluorine-containing aromatic compound represented by the following formula (2-1), the method including: reacting a compound represented by the following formula (1) with a compound represented by the formula $R_1$—$Si(CH_3)_3$ to obtain a compound represented by the following formula (1-1A), subjecting the compound represented by the formula (1-1A) to a deprotection treatment to obtain a compound represented by the following formula (1-1B), and aromatizing the compound represented by the formula (1-1B):

[Chem 7]

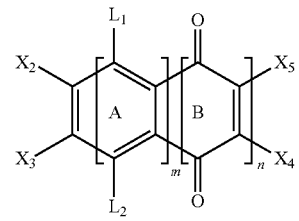
(1)

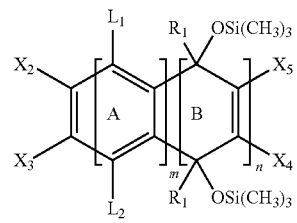
(1-1A)

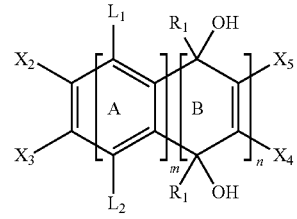
(1-1B)

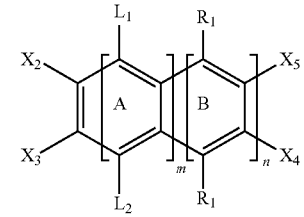
(2-1)

[In the formulae, $R_1$ is a linear perfluoroalkyl group having a carbon number of 1 to 3.

$X_2$ to $X_5$ are a halogen atom or a hydrogen atom and they may be the same or different.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent. $R_2$ to $R_5$ may be the same or different.

m and n are the numbers of repetitions of repeating unit structures A and B represented in parentheses, respectively, m is an integer of 0 or more, n is an integer of 1 or more, and m+n is an integer of 2 or more and 6 or less.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different. In the case where m is 2 or more, a plurality of the $L_1$ groups present in the structure A may be the same or different and a plurality of the $L_2$ groups present in the structure A may be the same or different.

In the case where at least one of m and n is 2 or more, the order of combining the structure A and the structure B may be block or random.]

<14>

A method for manufacturing a fluorine-containing aromatic compound represented by the following formula (2-2), the method including: replacing at least one of $X_2$ to $X_5$ as halogen atom(s), in a compound where at least one of $X_2$ to $X_5$ in a compound represented by the following formula (1) is a halogen atom, by a monovalent hydrocarbon group having a carbon number of 1 to 12 which may have a substituent, a monovalent aromatic hydrocarbon group which may have a substituent, or a monovalent heteroaromatic group which may have a substituent, subsequently reacting the compound after the replacement with a compound represented by the formula $R_1$—$Si(CH_3)_3$ to obtain a compound represented by the following formula (1-2A), subjecting the compound represented by the formula (1-2A) to a deprotection treatment to obtain a compound represented by the following formula (1-2B), and subsequently aromatizing the compound represented by the formula (1-2B):

[Chem 8]

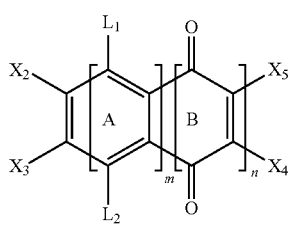

(1)

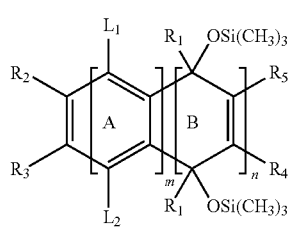

(1-2A)

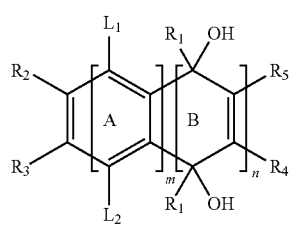

(1-2B)

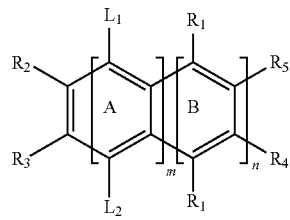

(2-2)

[In the formulae, $R_1$ is a linear perfluoroalkyl group having a carbon number of 1 to 3.

$X_2$ to $X_5$ are a halogen atom or a hydrogen atom and they may be the same or different.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent. $R_2$ to $R_5$ may be the same or different.

m and n are the numbers of repetitions of repeating unit structures A and B represented in parentheses, respectively, m is an integer of 0 or more, n is an integer of 1 or more, and m+n is an integer of 2 or more and 6 or less.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different. In the case where m is 2 or more, a plurality of the $L_1$ groups present in the structure A may be the same or different and a plurality of the $L_2$ groups present in the structure A may be the same or different.

In the case where at least one of m and n is 2 or more, the order of combining the structure A and the structure B may be block or random.]

Advantageous Effects of the Invention

Since the fluorine-containing aromatic compound obtained by the manufacturing method of the present invention has a small content of heavy metals, it is expected to have high carrier mobility as a charge transport material and an organic semiconductor thin film can be manufactured conveniently in large quantities for a short period of time. Namely, the fluorine-containing aromatic compound of the present invention can be utilized as an organic semiconductor material applicable to high-performance organic TFTs, organic EL elements, and the like.

MODES FOR CARRYING OUT THE INVENTION

The following will describe the present invention in detail but the present invention should not be construed as being limited to the following modes for carrying out the same and can be carried out with arbitrary modifications within the scope not deviating from the gist of the present invention.

Incidentally, a compound represented by the formula (X) is also referred to as a "compound (X)".

<Fluorine-Containing Aromatic Compound>

The fluorine-containing aromatic compound of the present invention is selected from a compound represented by the following formula (2-1) and a compound represented by the formula (2-2).

[Chem 9]

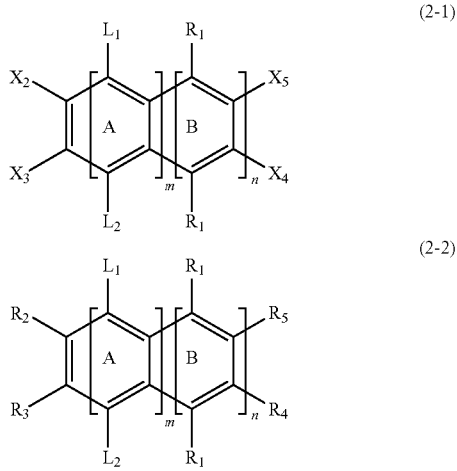

In the formulae, $R_1$ is a linear perfluoroalkyl group having a carbon number of 1 to 3.

$X_2$ to $X_5$ are a halogen atom or a hydrogen atom and they may be the same or different.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom; one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent; and $R_2$ to $R_5$ may be the same or different.

m and n are the numbers of repetitions of repeating unit structures A and B represented in parentheses, respectively, m is an integer of 0 or more, n is an integer of 1 or more, and m+n is an integer of 2 or more and 6 or less.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different; in the case where m is 2 or more, a plurality of the $L_1$ groups present in the structure A may be the same or different and a plurality of the $L_2$ groups present in the structure A may be the same or different.

In the case where at least one of m and n is 2 or more, the order of combining the structure A and the structure B may be block or random.

The fluorine-containing aromatic compound according to the present invention has a linear perfluoroalkyl group $R_1$ in a short axis direction of the compound, i.e., in a perpendicular direction to the condensation direction of the aromatic rings. A perfluoroalkyl group means a group in which all the hydrogen atoms of an alkyl group are replaced by fluorine atoms. In a condensed polycyclic compound, as the number of condensed rings increases, carrier mobility is expected to increase due to a strong intermolecular interaction resulting from π-π stacking. On the other hand, the strong intermolecular interaction also invites a decrease in solubility in organic solvents.

Since the compound of the present invention has 2n (n is an integer of 1 or more) groups of such linear perfluoroalkyl groups $R_1$ in the molecule, the solubility in organic solvents is remarkably enhanced. Moreover, the $R_1$ groups bonded to the same benzene ring are in a relationship of a para-position and this fact is preferable from the standpoints of an improvement in orientation toward a substrate and crystallinity of a thin film in the case where the fluorine-containing aromatic compound is used as an organic semiconductor material. Furthermore, the fact that the perfluoroalkyl group is a linear one is preferable in view of an improvement in the intermolecular interaction resulting from interaction of fluorine atoms.

The linear perfluoroalkyl group $R_1$ has a carbon number of 1 to 3. Namely, $R_1$ is a group selected from —$CF_3$, —$CF_2CF_3$, and —$CF_2CF_2CF_3$.

The longer the alkyl chain in $R_1$ is, the better the solubility in organic solvents is. Also, as the number of condensed rings increases, the carrier mobility is expected to increase due to a strong intermolecular interaction resulting from π-π stacking. In general, the strong intermolecular interaction resulting from the π-π stacking invites a decrease in solubility in organic solvents. However, in the present invention, as a result of investigation on the number of carbon atoms in the linear perfluoroalkyl group and the solubility of an acene material in organic solvents owing to the π-π stacking, it has been revealed that the solubility of the acene material in organic solvents is remarkably improved without impairing the strong intermolecular interaction resulting from the π-π stacking when the linear perfluoroalkyl group having a carbon number of 1 to 3 is introduced.

$R_1$ is particularly preferably a linear perfluoroalkyl group having a carbon number of 1 or 2, specifically a trifluoromethyl group or a pentafluoroethyl group. Incidentally, a plurality of the $R_1$ groups in the compound are the same.

2n (n is an integer of 1 or more) groups of the $R_1$ groups are present in the compound. With regard to $R_1$ in the case where n is 1, $R_1$ is preferably a linear perfluoroalkyl group having a carbon number of 2 to 3 in view of attaining the advantage effects of the present invention.

m and n are the numbers of repetitions of repeating unit structures A and B represented in parentheses, respectively, m is an integer of 0 or more, and n is an integer of 1 or more. m+n is an integer of 2 or more and 6 or less and, in view of achieving both of the solubility in organic solvents and the strong intermolecular interaction resulting from the π-π stacking, is preferably an integer of 3 or more and 6 or less.

In the case where at least one of m and n is 2 or more, the order of combining the structure A and the structure B may be block or random. The structure A and the structure B may be combined alternately.

$X_2$ to $X_5$ are a halogen atom or a hydrogen atom and they may be the same or different.

At least one of $X_2$ to $X_5$ is preferably a halogen atom. Thereby, a substituent can be further introduced into the fluorine-containing aromatic compound by replacing the halogen atom by $R_2$ to $R_5$. $R_2$ to $R_5$ in this case are a monovalent hydrocarbon group having a carbon number of 1 to 12 which may have a substituent, a monovalent aromatic hydrocarbon group which may have a substituent, or a monovalent heteroaromatic group which may have a substituent. As the halogen atom, preferred are a fluorine atom, a chlorine atom, a bromine atom, and an iodine atom and, from the standpoint of reactivity, a bromine atom and an iodine atom are particularly preferred. In the case of introducing a substituent into the fluorine-containing aromatic compound, one or two of $X_2$ to $X_5$ are preferably a halogen atom and, in the case of two halogen atoms, it is preferable that $X_3$ and $X_5$ or $X_2$ and $X_4$ are halogen atoms.

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent. $R_2$ to $R_5$ may be the same or different.

The monovalent hydrocarbon group having a carbon number of 1 to 12, the monovalent aromatic hydrocarbon group, and the monovalent heteroaromatic group each may have a substituent. Namely, one or more of the hydrogen atoms bonded to the carbon atoms in these groups may be replaced by group(s) selected from alkyl groups having a carbon number of 1 to 12, alkoxy groups having a carbon number of 1 to 12, perfluoroalkyl groups having a carbon number of 1 to 12, a phenyl group, and alkoxyphenyl groups having a carbon number of 7 to 12.

The monovalent hydrocarbon group having a carbon number of 1 to 12 in $R_2$ to $R_5$ is preferably an alkyl group having a carbon number of 1 to 12, an alkenyl group having a carbon number of 2 to 12, an alkynyl group having a carbon number of 2 to 12, or a cycloalkyl group having a carbon number of 3 to 12.

The alkyl group having a carbon number of 1 to 12 is preferably a group having a linear or branched structure and examples thereof include a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, an n-nonyl group, an n-decyl group, an n-dodecyl group, and the like.

As the alkenyl group having a carbon number of 2 to 12, a vinyl group, a propenyl group, a butenyl group, a pentenyl group, and the like may be mentioned. The position of the unsaturated bond is not limited but 1-position is preferred.

As the alkynyl group having a carbon number of 2 to 12, an acetyl group, a propynyl group, a butynyl group, a pentynyl group, and the like may be mentioned. The position of the unsaturated bond is not limited but 1-position is preferred.

As the cycloalkyl group having a carbon number of 3 to 12, a cyclopentyl group and a cyclohexyl group may be mentioned.

In the case where the monovalent hydrocarbon group having a carbon number of 1 to 12 has a substituent, as the substituent, there may be mentioned groups selected from alkoxy groups having a carbon number of 1 to 12, perfluoroalkyl groups having a carbon number of 1 to 12, a phenyl group, and alkoxyphenyl groups having a carbon number of 7 to 12. In this case, it is preferred to control the number of carbon atoms of the whole group including the substituent to 20 or less from the standpoint of the solubility in organic solvents.

The monovalent aromatic hydrocarbon group in $R_2$ to $R_5$ is a monovalent hydrocarbon group having aromaticity and a phenyl group is preferred.

In the case where the aromatic hydrocarbon group has a substituent, as the substituent, an electron-withdrawing or electron-donating substituent is preferred and specifically, there may be mentioned groups selected from alkoxy groups having a carbon number of 1 to 12 and perfluoroalkyl groups having a carbon number of 1 to 12. In the case where the monovalent aromatic hydrocarbon group is a phenyl group, the number of the substituents is preferably one and it is preferable that the substituent is present at the para-position of the phenyl group.

The monovalent heteroaromatic group in $R_2$ to $R_5$ is preferably a thienyl group. In the case where the heteroaromatic group has a substituent, as the substituent, there may be mentioned groups selected from alkyl groups having a carbon number of 1 to 12, alkoxy groups having a carbon number of 1 to 12, and perfluoroalkyl groups having a carbon number of 1 to 12. The number of the substituents is preferably one and it is preferable that the substituent is present at the 4- or 5-position of the thienyl group.

The halogen group in $R_2$ to $R_5$ is preferably a bromine atom or an iodine atom. In the case where $R_2$ to $R_5$ are halogen atom(s), at least one of $R_2$ and $R_4$ is preferably a halogen atom.

The fluorine-containing aromatic compound of the present invention is a compound in which a linear perfluoroalkyl group $R_1$ having a carbon number of 1 to 3 that is an electron-withdrawing substituent is introduced into an acene skeleton, and the solubility in organic solvents can be improved by further introducing $R_2$ to $R_5$. Since $R_2$ to $R_5$ introduced act as electron-withdrawing or electron-donating groups, electron transition energy can be controlled. As a result, it becomes possible to control conductivity and hence the compound is preferred as an organic semiconductor material. Accordingly, $R_2$ to $R_5$ are preferably a hydrogen atom, a monovalent hydrocarbon group having a carbon number of 1 to 12 which may have a substituent, a monovalent aromatic hydrocarbon group which may have a substituent, or a monovalent heteroaromatic group which may have a substituent. Furthermore, it is preferable that one group selected from $R_2$ to $R_5$ is a monovalent hydrocarbon group having a carbon number of 1 to 12 which may have a substituent, a monovalent aromatic hydrocarbon group which may have a substituent, or a monovalent heteroaromatic group which may have a substituent and remaining $R_2$ to $R_5$ are hydrogen atoms.

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different.

In the case where m is 2 or more, a plurality of the $L_1$ groups present in the structure A may be the same or different and a plurality of the $L_2$ groups present in the structure A may be the same or different.

In $L_1$ and $L_2$, the monovalent hydrocarbon group having a carbon number of 1 to 12 is preferably an alkyl group having a carbon number of 1 to 12 which has a linear structure or a branched structure and a cycloalkyl group having a carbon number of 3 to 12, the monovalent aromatic hydrocarbon group is preferably a phenyl group, the monovalent heteroaromatic group is preferably a thienyl group, and the halogen atom is preferably bromine or iodine.

In the case where $L_1$ and $L_2$ are groups having a substituent, as these groups, preferred is a phenyl group having an electron-withdrawing or electron-donating substituent and specifically, the groups exemplified in $R_2$ to $R_5$ may be mentioned. As $L_1$ and $L_2$, a hydrogen atom is preferred.

In the compound (2-1) or compound (2-2), from the standpoint of the strong intermolecular interaction resulting from the π-π stacking, preferred is a compound where m=2 and n=1, a compound where m=4 and n=1, or a compound where m=3 and n=2.

In the compound where m=2 and n=1, it is preferable that bonding positions of two $R_1$ groups are 9-position and 10-position of an acene skeleton in which three rings are condensed and $L_1$ and $L_2$ are hydrogen atoms. Namely, the following compound (3-1) or the following compound (3-2) is preferred.

[Chem 10]

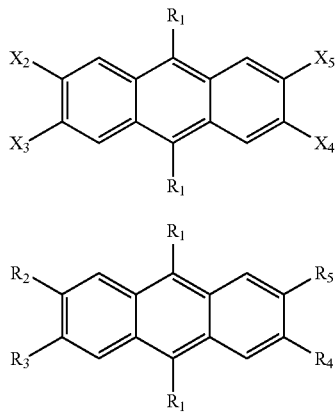

(3-1)

(3-2)

In the formula (3-1) and formula (3-2), $X_2$ to $X_5$ and $R_1$ to $R_5$ represent the same meaning as mentioned above. Preferably, $X_2$ to $X_5$ are a bromine atom, an iodine atom, or a hydrogen atom, and more preferably, at least one thereof is a bromine atom or an iodine atom. It is preferable that one or more of $R_2$ to $R_5$ are an alkynyl group having a carbon number of 1 to 12, an alkynyl group having a carbon number of 1 to 12 which has a substituent, a phenyl group, a phenyl group which has a substituent, a thienyl group, a bromine atom, or an iodine atom and the remainder are hydrogen atoms. More preferred is the case where at least one of $R_2$ and $R_4$ in $R_2$ to $R_5$ is an alkynyl group having a carbon number of 1 to 12, an alkynyl group having a carbon number of 1 to 12 which has a substituent, a phenyl group, a phenyl group which has a substituent, a thienyl group, a bromine atom, or an iodine atom and the remainder are hydrogen atoms.

Moreover, in the compound where m=4 and n=1, it is preferable that bonding positions of two $R_1$ groups are 6-position and 13-position of an acene skeleton in which five rings are condensed and $L_1$ and $L_2$ are hydrogen atoms. Namely, the following compound (4-1) or the following compound (4-2) is preferred.

[Chem 11]

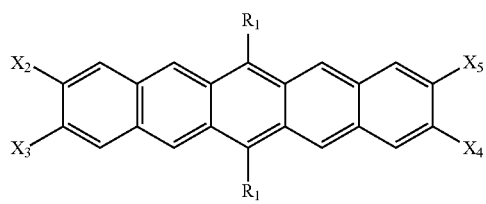

(4-1)

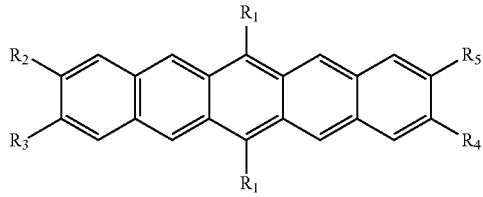

(4-2)

Furthermore, in the compound where m=3 and n=2, it is preferable that bonding positions of four $R_1$ groups are 5-, 7-, 12- and 14-positions of an acene skeleton in which five rings are condensed and $L_1$ and $L_2$ are hydrogen atoms. Namely, the following compound (5-1) or the following compound (5-2) is preferred.

[Chem 12]

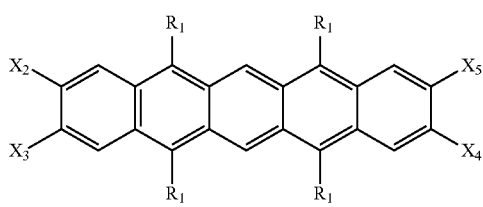

(5-1)

(5-2)

In the formula (4-1), formula (4-2), formula (5-1), and formula (5-2), $R_1$ represents the same meaning as mentioned above and preferable embodiments and more preferable embodiments are also the same. $X_2$ to $X_5$ represent the same meanings as mentioned above, and preferable embodiments are the same as in the formula (3-1) and more preferred is a hydrogen atom. $R_2$ to $R_5$ represent the same meanings as mentioned above, and preferable embodiments and more preferable embodiments are the same as in the formula (3-2).

As the compound (2-1) and compounds (2-2), specifically, preferred are compounds selected from the compound group represented by the following formulae.

[Chem 13]

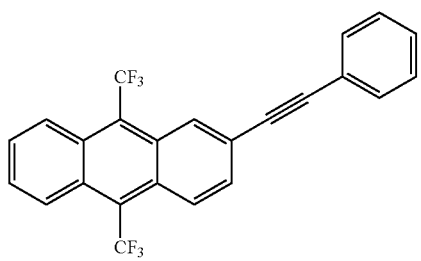

-continued
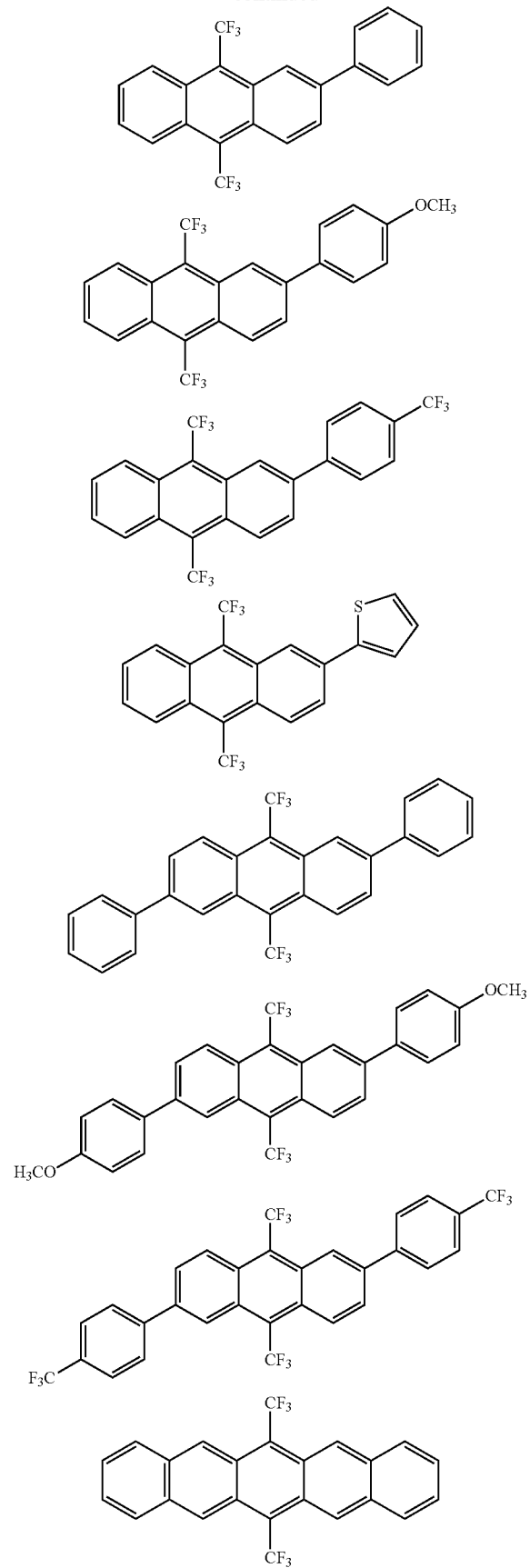
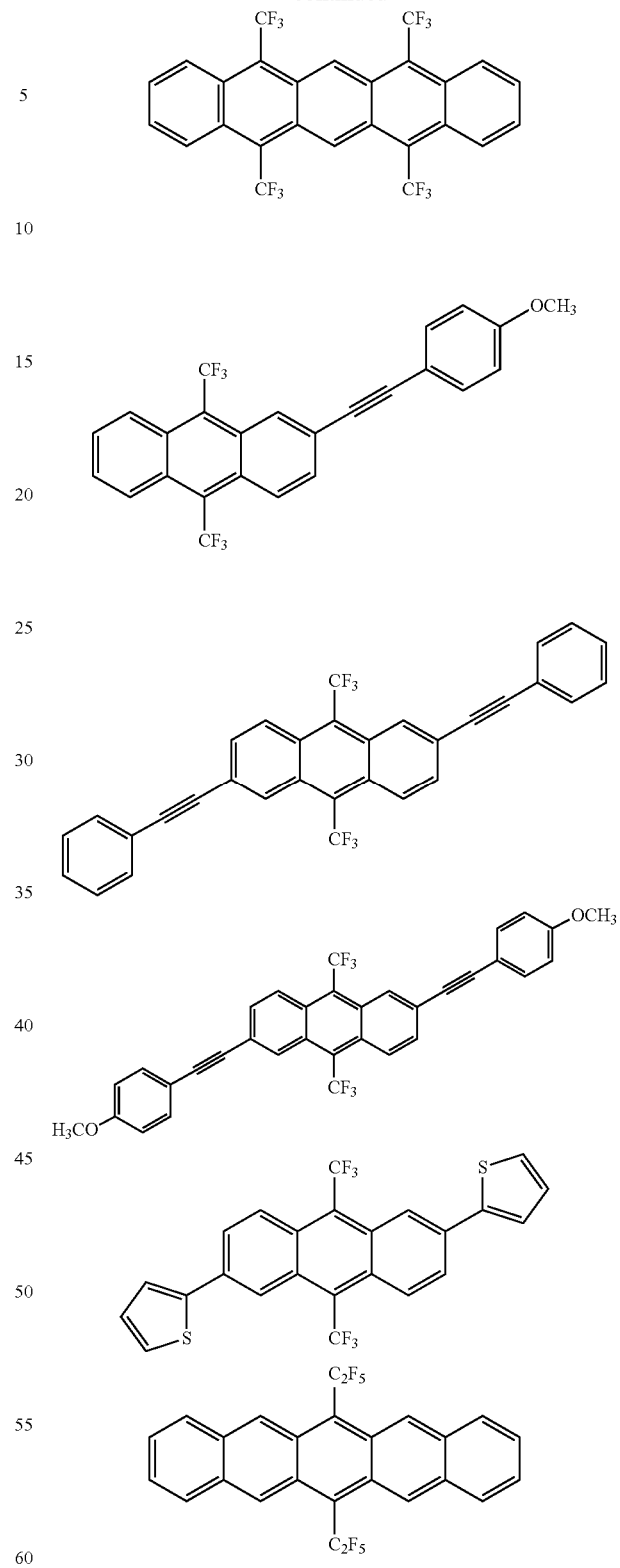
<Manufacturing Method of Fluorine-Containing Aromatic Compound and Intermediate>
Next, a summary of manufacturing routes of the fluorine-containing aromatic compound of the present invention can be shown in the following.

[Chem 14]

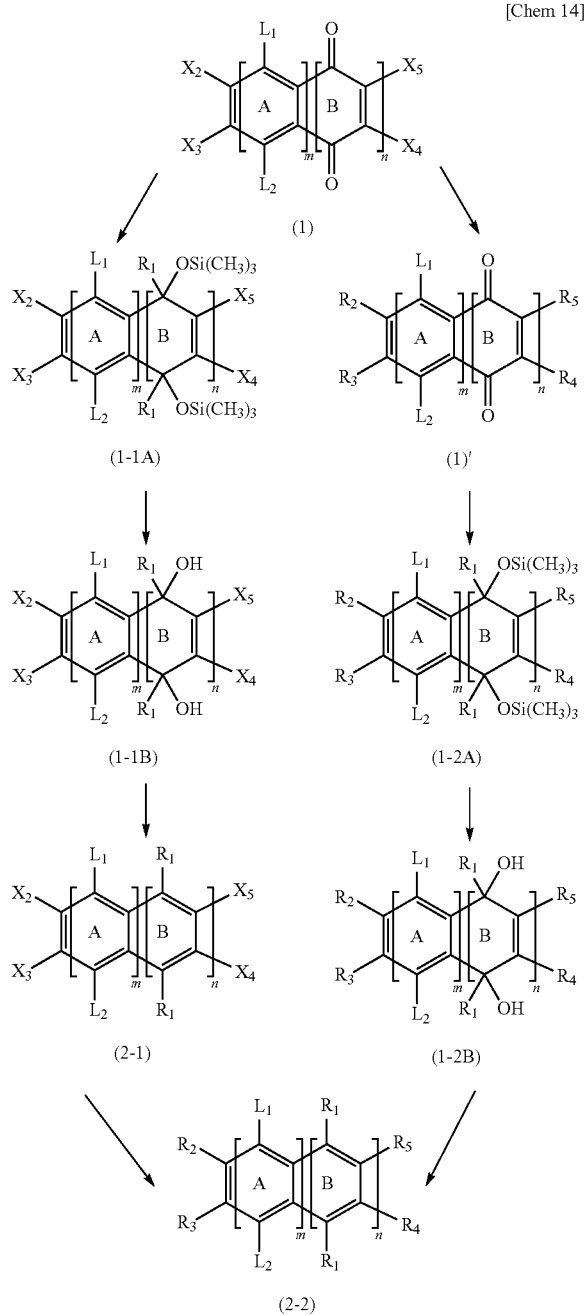

In the manufacturing method of the present invention, the quinone compound (1) is used as a starting material and steps of introducing $R_1$, i.e., steps of converting the keto groups in the quinone into C—$R_1$ groups are essential. $R_1$ is a linear perfluoroalkyl group having a carbon number of 1 to 3.

Furthermore, in the case where at least one of $X_2$ to $X_5$ of the quinone compound (1) is a halogen atom, a reaction of replacing $X_2$ to $X_5$ as halogen atom(s) by $R_2$ to $R_5$ may be carried out. Thereby, a desired substituent can be introduced. A part or all of $X_2$ to $X_5$ as halogen atom(s) are replaced. $R_2$ to $R_5$ in the case where they are introduced are a monovalent hydrocarbon group having a carbon number of 1 to 12 which may have a substituent, a monovalent aromatic hydrocarbon group which may have a substituent, or a monovalent heteroaromatic group which may have a substituent and remaining $R_2$ to $R_5$ are halogen atom(s) or hydrogen atom(s) corresponding to original $X_2$ to $X_5$.

The reaction of replacing the halogen atom may be carried out before the conversion of the keto groups into the C—$R_1$ groups, i.e., a compound (1)' may be obtained from the compound (1) or the reaction may be carried out after the conversion, i.e., after a compound (1-1A) is obtained from the compound (1).

The following will describe the manufacturing method of the present invention by using an embodiment of performing the replacement of the halogen atom after the introduction of $R_1$ as an example.

First, in order to replace the keto groups of the quinone into the C—$R_1$ groups, the compound (1) is reacted with a compound represented by $R_1$—Si(CH$_3$)$_3$ to obtain an intermediate compound (1-1A). Subsequently, the compound (1-1A) is subjected to a deprotection treatment to obtain an intermediate compound (1-1B). Furthermore, by aromatizing the compound (1-1B), a fluorine-containing aromatic compound (2-1) can be obtained. By the above steps, the keto groups are converted into the C—$R_1$ groups. According to this reaction, all the keto groups are converted into the same C—$R_1$ groups by one-time reaction.

As the compound (1) that is a starting material, known quinone-based compounds can be used and the following compound are preferred.

[Chem 15]

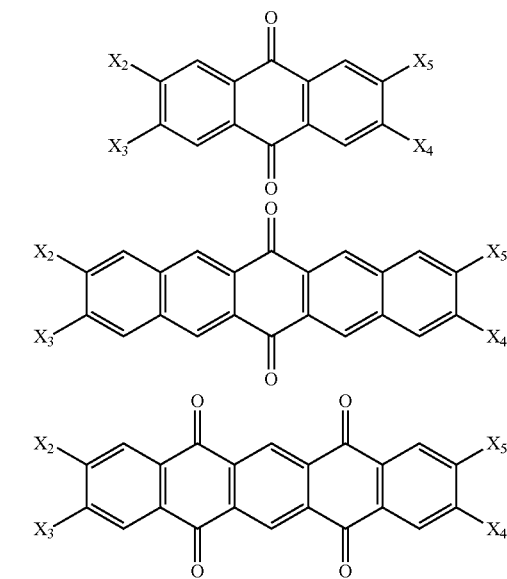

Specifically, as the compound (1), there may be mentioned 9,10-anthraquinone, 2-bromo-9,10-anthraquinone, 2-iodo-9,10-anthraquinone, 2,6-dibromo-9,10-anthraquinone, 2,6-diiodo-9,10-anthraquinone, 6,13-pentacenequinone, 5,7,12,14-tetrahydropentacene-5,7,12,14-tetraone, and the like.

The compound represented by $R_1$—Si(CH$_3$)$_3$ (hereinafter "—Si(CH$_3$)$_3$" is also described as "TMS") to be reacted with the compound (1) is preferably used in an amount of 2.0 to 2.5 mol/g-equivalent to the compound (1). Furthermore, a carbonate salt is added in an amount of 0.3 to 0.4 mol/g-equivalent to the compound (1) and reaction is carried out in an organic solvent at room temperature for 6 to 18 hours to obtain the compound (1-1A).

As the carbonate salt, alkali carbonate salts and the like may be mentioned and, of these, potassium carbonate is particularly preferred. As the organic solvent, amide-based solvents and the like may be mentioned and, of these, N,N-dimethylformamide is preferred.

The reaction method for deprotecting the TMS group of the compound (1-1A) to convert it into an alcohol compound (1-1B) is not limited and, for example, a deprotection reaction by an acid treatment using concentrated hydrochloric acid may be mentioned. In this case, for example, preferred is a method in which concentrated hydrochloric acid is added in an amount of 1 to 5 mol/g-equivalent to the compound (1-1A) and reaction is carried out in an organic solvent under reflux for 3 to 24 hours.

The organic solvent is preferably a water-soluble organic solvent and ethanol and tetrahydrofuran are particularly preferred.

The deprotection of the TMS group can be also carried out by using a fluoride source such as tetrabutylammonium fluoride. Preferred is a method in which tetrabutylammonium fluoride is added in an amount of 1 to 5 mol/g-equivalent to the compound (1-1A) and reaction is carried out in an organic solvent at 0° C. for 0.5 to 5 hours. When the TMS group is deprotected, an alcohol compound (1-1B) is obtained.

Also for the aromatization of the compound (1-1B), a known method is applicable without limitation but, in the present invention, it is preferred not to apply a method using a heavy metal (e.g., tin chloride) that is used in a general aromatization reaction. The aromatization is preferably an aromatization via elimination of a hydroxyl group by a thermal treatment at 220° C. or higher under vacuum. Moreover, for example, preferred is an aromatization reaction via an elimination step of a hydroxyl group using triphenylphosphine/carbon tetrabromide. Specifically, carbon tetrabromide is added to the compound (1-1B) in an amount of 3 to 10 mol/g-equivalent to the compound (1-1B) in an organic solvent, the whole is kept at 0° C., triphenylphosphine is further added thereto in an amount of 2 to 10 mol/g-equivalent to the compound (1-1B), and reaction is carried out under reflux for 3 to 24 hours in the organic solvent.

The organic solvent is preferably a chlorinated solvent. Dichloromethane, chloroform, and carbon tetrachloride may be mentioned, and dichloromethane is particularly preferred.

By the above reaction, the compound (2-1) is formed.

In the compound (2-1), in the case where at least one of $X_2$ to $X_5$ is a halogen atom, a desired substituent is introduced into the compound (2-1) by replacing $X_2$ to $X_5$ as halogen atom(s) by $R_2$ to $R_5$ and thereby, the compound (2-2) can be obtained. For the method, a reaction of forming a C—C bond from a C—X bond is applicable, and the Suzuki coupling reaction and the Sonogashira coupling reaction may be mentioned.

By the above reaction, the fluorine-containing aromatic compound (2-1) or the fluorine-containing aromatic compound (2-2) can be obtained.

As another method for obtaining the fluorine-containing aromatic compound (2-2), there is a method in which the step of replacing the halogen atom is conducted before the step of converting the keto groups into the C—$R_1$ groups. Namely, in the case where at least one of $X_2$ to $X_5$ in the compound (1) is a halogen atom, $X_2$ to $X_5$ as halogen atom(s) are replaced by any of $R_2$ to $R_5$ to obtain the compound (1)'.

Subsequently, the reactions of converting the keto groups of the quinone into the C—$R_1$ groups are successively conducted. Namely, the compound (1)' is reacted with the compound represented by $R_1$—Si(CH$_3$)$_3$ to obtain an intermediate compound (1-2A). Subsequently, the compound (1-2A) is subjected to a deprotection treatment to obtain an intermediate compound (1-2B). Furthermore, by aromatizing the compound (1-2B), the fluorine-containing aromatic compound (2-2) can be obtained.

Conditions for the step of replacing the halogen atom and the step of converting the keto groups into the C—$R_1$ groups are the same as in the embodiment in which the above replacement of the halogen atom is conducted after the introduction of $R_1$.

According to the synthetic method of the fluorine-containing aromatic compound in the present invention, a coupling reaction using a heavy metal is not used at the time of introducing the linear perfluoroalkyl group $R_f$ having a carbon number of 1 to 3, so that the ratio of the heavy metal contained in the synthesized compound can be reduced. Namely, in the fluorine-containing aromatic compound obtained by the method of the present invention, the amount of heavy metals contained in the compound can be made to 25 ppm by weight or less and preferably 20 ppm by weight or less.

<Organic Semiconductor Material>

The organic semiconductor material of the present invention means a material which contains the fluorine-containing aromatic compound of the present invention and is to be used as an organic semiconductor. The organic semiconductor material of the present invention may be composed of the fluorine-containing aromatic compound of the present invention alone or may contain other components. As the other components, for example, other organic semiconductor materials and various dopants may be mentioned. As the dopant, for example, in the case of being used as a light-emitting layer of an organic EL element, coumarin, quinacridone, rubrene, stilbene-based derivatives, fluorescent dyes, and the like can be used.

The fluorine-containing aromatic compound of the present invention has a melting point of lower than about 300° C. This is considered to be attributable to the fact that, in the linear perfluoroalkyl group $R_1$ having a carbon number of 1 to 3, thermal movement owing to the chain length weakens the crystallinity between the molecules.

Moreover, it is considered that the presence of the linear perfluoroalkyl group $R_1$ having a carbon number of 1 to 3 stabilizes a molecular arrangement (π-π stacking) where the planes of the aromatic rings as a main skeleton face each other, and thus contributes to the realization of the charge mobility as compared with unsubstituted one.

Moreover, the linear perfluoroalkyl groups having a carbon number of 1 to 3 located at 9- and 10-positions in the case of anthracene and at 6- and 13-positions in the case of pentacene have two roles, i.e., a role of blocking dimerization of the pentacene compounds themselves at the position and a role of preventing deterioration behavior of transforming into a quinone skeleton such as anthraquinone or pentacenequinone, which may be caused by oxygen or moisture in the air. Furthermore, also in the case where pentacene has the linear perfluoroalkyl groups having a carbon number of 1 to 3 at 4-, 7-, 12-, and 14-positions, deterioration derived from the quinone skeleton at 6- and 13-positions is prevented by steric repulsion of these substituents.

Furthermore, adjacent molecules are aggregated by affinity between the linear perfluoroalkyl groups having a carbon number of 1 to 3 (a fluorophilic effect), so that the groups contribute to more efficient charge transfer. Therefore, when the fluorine-containing aromatic compound of the present invention is used, the preparation of an organic semiconductor thin film maintaining high carrier mobility and an electronic element utilizing the same, such as a transistor, can be realized.

Usually, anthracene and pentacene having no substituent act as p-type semiconductors. However, the fluorine-containing aromatic compound of the present invention having the linear perfluoroalkyl groups $R_1$ having a carbon number of 1 to 3 that is an electron-withdrawing substituent introduced thereinto has a possibility that conductivity changes depending on the substituent. Accordingly, in the fluorine-containing aromatic compound of the present invention, the linear perfluoroalkyl group $R_1$ having a carbon number of 1 to 3 in a part of the acene skeleton can control the conductive type as a result of a change in the electron transition energy, so that the compound is preferable as an organic semiconductor material.

<Organic Semiconductor Thin Film>

The organic semiconductor material according to the present invention can form an organic semiconductor film on a substrate according to a usual manufacturing method using a dry process or a wet process. As the film, a thin film, a thick film, or a film having crystallinity may be mentioned.

In the case of forming a thin film by a dry process, there may be used a known method such as a vacuum deposition method, an MBE (Molecular Beam Epitaxy) method, a sputtering method, a laser deposition method, or a vapor-phase transport growth method.

These thin films and the like function as charge transport members of various functional elements such as a photoelectric conversion element, a thin-film transistor element, and a light-emitting element, and thus it is possible to prepare a variety of electronic devices by using the semiconductor material.

In the case where the thin film is formed by using the vacuum deposition method, the MBE method, or the vapor-phase transport growth method as a dry process, the organic semiconductor material is heated and sublimed vapor is transported to the substrate surface under high vacuum, vacuum, low vacuum, or normal pressure. The formation of the thin film can be carried out according to known methods or conditions. Specifically, substrate temperature is preferably from 20 to 200° C. and a thin-film growth rate is preferably from 0.001 to 1,000 nm/sec. Under such conditions, a film having crystallinity and having surface smoothness of the thin film can be formed.

When the substrate temperature is a low temperature, the thin film is prone to be amorphous, while when the temperature is a high temperature, the surface smoothness of the thin film tends to decrease. Further, when the thin-film growth rate is low, the crystallinity is prone to decrease, while when the rate is too high, the surface smoothness of the thin film tends to decrease.

In the case of forming the thin film by a wet process, the organic semiconductor thin film can be formed by covering a substrate with a solution obtained by dissolving the organic semiconductor material containing the fluorine-containing aromatic compound in an organic solvent.

The fluorine-containing aromatic compound of the present invention is a compound having an improved solubility in organic solvents as compared with conventional organic semiconductor materials and having an advantage that a wet process is applicable. The reason is that the organic semiconductor material according to the present invention exhibits lipophilicity owing to the presence of the perfluoroalkyl group in the fluorine-containing aromatic compound, so that the material becomes soluble in various organic solvents. The film formation by a wet process has the advantage of being able to process without damaging semiconductor crystals.

As film formation methods in a wet process (methods for covering a substrate), coating, spraying, and contact, and the like may be mentioned. Specifically, there may be mentioned known methods such as a spin coating method, a casting method, a dip coating method, an ink-jet method, a doctor blade method, a screen printing method, and a dispense method. Moreover, in the case of a plate-like crystal or a thick-film state, the casting method or the like can be adopted. As the film formation method and the organic solvent, it is preferable to select a suitable combination for the device to be prepared.

In the wet process, crystal growth can be controlled by imparting at least one selected from temperature gradient, electric field, and magnetic field to the interface between the solution of the fluorine-containing aromatic compound and the substrate. When such a method is adopted, an organic semiconductor thin film having a higher crystallinity can be manufactured and excellent semiconductor properties based on the performance of the thin film having a high crystallinity can be obtained. Moreover, also by adopting a solvent atmosphere as the environmental atmosphere at the time of the wet-process film formation, an organic semiconductor thin film having a high crystallinity can be manufactured with controlling the vapor pressure in solvent drying.

In the wet process, as examples of the organic solvent in which the fluorine-containing aromatic compound can be dissolved, there may be mentioned examples of non-halogen solvents, for example, aliphatic hydrocarbons such as pentane, hexane, and heptane; alicyclic hydrocarbons such as cyclohexane; aromatic hydrocarbons such as benzene, toluene, xylene, phenol, and cresol; ethers such as diethyl ether, tert-butyl methyl ether, tetrahydrofuran, and dioxane; alcohols such as methanol, ethanol, and 2-propanol; mixtures thereof; and the like.

As examples of halogen-containing solvents, there may be exemplified chlorinated hydrocarbons, chlorinated aromatic hydrocarbons, fluorinated hydrocarbons, chlorinated fluorinated hydrocarbons, and fluorine-containing ether compounds. Specifically, there may be mentioned methylene chloride, chloroform, 1,2-dichloroethane, chlorobenzene, 1,2-dichlorobenzene, 1,2,4-trichlorobenzene, 2,3,3-trichloroheptafluorobutane, 1,1,1,3-tetrachloro-2,2,3,3-tetrafluoropropane, 1,1,1-trichloropentafluoropropane, 1,1-dichloro-2,2,3,3,3-pentafluoropropane, 1,3-dichloro-1,1,2,2,3-pentafluoropropane, carbon tetrachloride, 1,2-dichloroethane, dichloropentafluoropropane, n-$C_6F_{13}$— $C_2H_5$, n-$C_4F_9OCH_3$, n-$C_4F_9OC_2H_5$, and the like.

Only one kind of the solvent may be used or two or more kinds thereof may be used in combination. In the case of using two or more kinds thereof in combination, it is preferred to use a non-halogen solvent and a halogen-containing solvent in combination, and a solvent obtained by mixing them in an arbitrary ratio is preferred.

In the case of performing the wet process with dissolving the fluorine-containing aromatic compound of the present invention in an organic solvent, from the standpoints of work efficiency and the like, the concentration of the organic semiconductor material to be dissolved in the organic solvent is preferably 0.01% by weight or more, particularly preferably from 0.01 to 10% by weight and especially preferably from 0.2 to 10% by weight in the organic solvent. Since the fluorine-containing aromatic compound of the present invention is excellent in solubility in organic solvents, it is also suitable to use the compound after the fluorine-containing aromatic compound obtained by the above manufacturing method is made highly pure by a simple and easy purification method such as column chromatography or recrystallization.

The covering of the substrate by the wet process can be performed under the atmospheric air or under an inert gas atmosphere. Particularly, in the case where the solution of the semiconductor material is easily oxidized, the covering is preferably performed under an inert gas atmosphere, and nitrogen, argon, or the like can be used.

After the substrate is covered, by evaporating the solvent, an organic semiconductor thin film is formed. When an amount of the remaining solvent in the thin film is large, there is a concern that stability and semiconductor properties of the thin film decrease. Therefore, it is preferable to remove the remaining solvent by performing a heat treatment or a pressure-reducing treatment again after the thin film formation.

The shape of the substrate usable in the wet process is not particularly limited and usually, a sheet-like substrate or a plate-like substrate is preferred. The material to be used as the substrate is also not particularly limited, and ceramics, metal substrates, semiconductors, resins, paper, nonwoven fabrics, and the like may be mentioned.

As examples in the case where the substrate is a ceramic substrate, there may be mentioned substrates of glass, quartz, aluminum oxide, sapphire, silicon nitride, silicon carbide, and the like. As the metal substrate, substrates of gold, copper, silver, and the like may be mentioned. As the semiconductor substrate, there may be mentioned substrates of silicon (crystalline silicon, amorphous silicon), germanium, gallium arsenide, gallium phosphide, gallium nitride, and the like. As the resin substrate, there may be mentioned substrates of polyester, polyethylene, polypropylene, polyvinyl, polyvinyl alcohol, ethylene-vinyl alcohol copolymer, cyclic polyolefin, polyimide, polyamide, polystyrene, polycarbonate, polyether sulfone, polysulfone, polymethyl methacrylate, polyethylene terephthalate, triacetylcellulose, norbornene, and the like.

By using the fluorine-containing aromatic compound, the resulting organic semiconductor thin film can be made a crystalline thin film. A crystalline thin film is preferable since high carrier mobility is expectable owing to the high crystallinity and thereby excellent organic semiconductor device properties are realized.

A crystalline state of the thin film can be known by grazing incidence X-ray diffraction measurement of the thin film, transmission electron beam diffraction, or a method of allowing X-ray to enter into an edge part of the thin film to measure diffraction. Particularly, it is preferred to use the grazing incidence X-ray diffraction that is a crystal analysis method in the thin film field.

As the X-ray diffraction method, there are an Out-of-plane XRD method and an In-plane XRD method depending on the direction of a lattice plane to be measured. The Out-of-plane XRD method is a method of observing a lattice plane parallel to the substrate. The In-plane XRD method is a method of observing a lattice plane perpendicular to the substrate.

The fact that a thin film has crystallinity means that diffraction peak(s) derived from the organic semiconductor material forming the thin film are observed. Specifically, it means that there are observed diffraction based on a crystal lattice of the organic semiconductor material, diffraction derived from molecular length, or characteristic diffraction peak(s) appearing at the time when molecules have an orientation of arranging parallel or perpendicular to the substrate. In the case of a film in a non-crystalline state, the diffraction is not observed and thus a thin film appearing diffraction peak(s) means that the film is a crystalline thin film.

Thickness of the organic semiconductor thin film layer for use in an organic semiconductor element is usually preferably from 10 to 1,000 nm.

<Organic Semiconductor Element, Organic Semiconductor Transistor>

The fluorine-containing aromatic compound of the present invention has high carrier mobility. Accordingly, an organic semiconductor material containing the same can form an organic semiconductor thin film without impairing the high carrier mobility of the fluorine-containing aromatic compound.

An organic semiconductor element containing a semiconductor layer formed by stacking layers of the organic semiconductor thin film is very useful for various semiconductor devices.

Examples of the semiconductor devices include organic semiconductor transistors, organic semiconductor lasers, organic photoelectric conversion devices, organic molecular memories, and the like. Of these, as the semiconductor device, an organic semiconductor transistor is preferred and further, a field effect transistor (FET) is more preferred.

The organic semiconductor transistor is usually composed of a substrate, a gate electrode, an insulator layer (dielectric layer), a source electrode, a drain electrode, and a semiconductor layer. Besides, a back gate, a bulk, and the like may be included.

The order and the like of disposing the constituent elements in the organic semiconductor transistor are not particularly limited. Moreover, of the above constituent elements, the gate electrode, source electrode, drain electrode, and semiconductor layer may be provided as those each composed of plural layers. In the case where plural layers of semiconductor layer are present, the layers may be provided in the same plane or may be provided by stacking them.

As above, the fluorine-containing aromatic compound of the present invention has high carrier mobility and has excellent properties as a semiconductor material. As mentioned above, since the fluorine-containing aromatic compound of the present invention has a high solubility in organic solvents, a simple and convenient film formation process such as a casting method or a printing method can be utilized, so that the organic semiconductor thin film or the organic semiconductor element can be manufactured without impairing the high carrier mobility of the fluorine-containing aromatic compound.

Moreover, the compound (1-2A) or the compound (1-2B) of the present invention can be utilized as a conversion-type precursor material of a coating-type organic semiconductor material. Specifically, when a solution thereof dissolved in an organic solvent as a precursor of the fluorine-containing aromatic compound (2-2) of the present invention is applied on a substrate and then a thermal treatment at 220° C. or higher is conducted under vacuum, it can be converted into the fluorine-containing aromatic compound (2-2) of the present invention. By this method, an organic semiconductor thin film or organic semiconductor element of the fluorine-containing aromatic compound can be manufactured.

EXAMPLES

The following will specifically describe the present invention with reference to Examples but the present invention should not be construed as being limited to these Examples.

Moreover, in the present Examples, structure determination of compounds was performed by the analytical methods shown below.

For nuclear magnetic resonance analysis, a Fourier transform high resolution nuclear magnetic resonance apparatus (NMR), JNM-AL400 manufactured by JEOL Ltd. was used.

¹H-NMR (300 MHz) solvent: chloroform-d (CDCl₃), methanol-d₄ (CD₃OD), or acetone-d₆ (Acetone-d₆), internal standard: tetramethylsilane (TMS).

¹³C-NMR (75 MHz) solvent: chloroform-d (CDCl₃), methanol-d₄ (CD₃OD), or acetone-d₆ (Acetone-d₆), internal standard: chloroform-d (CDCl₃).

¹⁹F NMR (283 MHz) solvent: chloroform-d (CDCl₃), methanol-d₄ (CD₃OD), or acetone-4 (Acetone-d₆), internal standard: hexafluorobenzene (C₆F₆) was regarded as −163 ppm (CFCl₃ being regarded as 0 ppm).

For infrared absorption spectroscopy, a Fourier transform infrared spectrophoto altimeter (FT-IR), FT/IR-4100 manufactured by JASCO Corporation was used.

For elemental analysis, a full automatic elemental analysis apparatus 2400 Series II manufactured by PerkinElmer Co., Ltd. was used.

For melting point measurement, a melting point meter MP-21 manufactured by Yamato Scientific Co., Ltd. was used.

For HRMS, JMS-700 manufactured by JEOL Ltd. was used, and measurement was conducted in a positive charge mode.

For fluorescent spectrum, a spectrophotofluoro meter (FP-6500) manufactured by JEOL Ltd. was used.

Example 1-a

Synthesis of Compound (a)

CF₃TMS (manufactured by Tosoh F-Tech, Inc., 3.30 mL, 22 mmol) was added to an N,N-dimethylformamide (manufactured by Wako Pure Chemical Industries, Ltd., 20 mL) solution of 9,10-anthraquinone (manufactured by Tokyo Chemical Industry Co., Ltd., 2.082 g, 10 mmol) and potassium carbonate (manufactured by Kanto Chemical Co., Inc., 0.553 g, 4.0 mmol) at 0° C., followed by stirring at room temperature for 15 hours. Thereafter, the reaction mixture was poured into a mixture of an aqueous saturated ammonium chloride solution (15 mL) and 1N HCl (5.0 mL), followed by extracting with diethyl ether. After the obtained organic layer was dried over anhydrous sodium sulfate, the organic solvents were removed by using a rotary evaporator. A crude product was purified by a column chromatography (manufactured by Kanto Chemical Co., Inc., silica gel 60 (spherical, 63-210 μm), developing solvent: hexane). The objective compound (a) (4.039 g, 82% yield) was obtained as a white solid.

(Analytical Results)
m.p. 118-120° C.
¹H NMR δ −0.10 (s, 18H), 7.48-7.55 (m, 4H), 7.93-7.99 (m, 4H).
¹³C NMR δ 1.7, 75.9 (q, J=27.9 Hz), 125.7 (q, J=289.0 Hz), 130.0, 130.7 (q, J=3.1 Hz), 134.1.
¹⁹F NMR δ −79.29 (s).
IR (KBr) ν 3073, 2968, 1487, 1447, 1441, 1237, 1175, 1075, 944, 930, 876, 846 cm⁻¹.
Anal. Calcd for: C, 53.64; H, 5.32. Found: C, 53.54; H, 5.38.

[Chem 16]

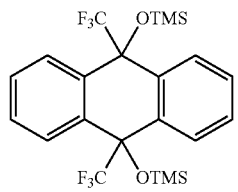

(a)

Example 1-b

Synthesis of Compound (b)

The compound (a) (3.541 g, 7.2 mmol) was dissolved in ethanol (15 mL) and concentrated hydrochloric acid (manufactured by Wako Pure Chemical Industries, Ltd., 2.0 mL, 24 mmol) was added thereto, followed by refluxing. After 3 hours, the reaction mixture was poured into an aqueous saturated ammonium chloride solution (20 mL) and a crude product was extracted with ethyl acetate. After the obtained organic layer was dried over anhydrous sodium sulfate, the solvents were removed by using a rotary evaporator. A crude product was purified by a column chromatography (developing solvent: hexane/ethyl acetate=2:1). The objective compound (b) (2.198 g, 88% yield) was obtained as a white solid.

(Analytical Results)
m.p. 197-199° C.
¹H NMR (Acetone-d₆) δ 6.52-6.54 (m, 2H), 7.55-7.63 (m, 4H), 8.02-8.16 (m, 4H).
¹³C NMR (Acetone-d₆) δ 73.7 (q, J=27.3 Hz), 125.7 (q, J=287.8 Hz), 129.4 (q, J=3.1 Hz), 129.7, 135.0.
¹⁹F NMR (Acetone-d₆) δ −76.98 (s).
IR (KBr) ν 3534, 3078, 1658, 1488, 1450, 1333, 1212, 1176, 1042, 912 cm⁻¹.
Anal. Calcd for: C, 53.64; H, 5.32. Found: C, 53.54; H, 5.38.

[Chem 17]

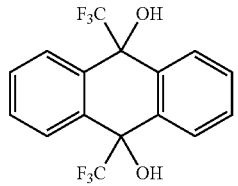

(b)

Example 1-c

Synthesis of Compound (c) (Reference Example)

Triphenylphosphine (manufactured by Kanto Chemical Co., Inc., 0.367 g, 1.4 mmol) was added to a dichloromethane (manufactured by Kanto Chemical Co., Inc., 2.0 mL) solution of the compound (b) (0.104 g, 0.3 mmol) and carbon tetrabromide (manufactured by Tokyo Chemical Industry Co., Ltd., 0.298 g, 0.9 mmol) at 0° C., followed by stirring at room temperature for 15 hours. After 15 hours, the reaction mixture was poured into an aqueous saturated ammonium chloride solution (20 mL) and a crude product was extracted with dichloromethane. After the obtained organic layer was dried over anhydrous sodium sulfate, the solvent was removed by using a rotary evaporator. A crude product was purified by a column chromatography (developing solvent: hexane). The objective compound (c) (0.062 g, 66% yield) was obtained as a yellow solid.

(Analytical Results)

m.p. 152-154° C.

$^1$H NMR δ 7.56-7.64 (m, 4H), 8.45-8.56 (m, 4H).

$^{19}$F NMR δ −49.81 (s).

IR (KBr) ν 3153, 3097, 3047, 1535, 1450, 1379, 1289, 1210, 1184, 1126, 1105, 956, 765, 675 cm$^1$.

HRMS (APCI). found: m/z 314.0504. Calcd for $C_{16}H_8F_6$ (M$^+$): 314.0530

[Chem 18]

(c)

Example 2-a

Synthesis of Compound (d)

The same operations were performed except that anthraquinone in Example 1-a was changed to 2-bromoanthraquinone (1.57 g, 4.68 mmol) and stirring was conducted at room temperature for 12 hours. After 12 hours, the reaction mixture was poured into an aqueous saturated ammonium chloride solution and 1N HCl, and a crude product was extracted with diethyl ether. After the obtained organic layer was dried over anhydrous sodium sulfate, the solvents were removed by using a rotary evaporator. Ethanol (10 mL) and concentrated hydrochloric acid (1 mL) were added to a crude product obtained by concentration, followed by refluxing for 3 hours. An aqueous saturated ammonium chloride solution was added thereto, followed by extracting with ethyl acetate, drying over anhydrous magnesium sulfate and concentrating. A crude product was purified by a column chromatography (developing solvent: hexane/ethyl acetate=2:1). The objective compound (d) (2.018 g, 91% yield) was obtained as a white solid.

(Analytical Results)

$^1$H NMR δ 8.19 (1H, t, J=2.1 Hz), 8.04-8.01 (2H, m), 7.91 (1H, dq, J=8.7, 2.3 Hz), 7.71 (1H, dd, J=2.1 Hz), 7.60 (2H, dd, J=3.3, 6.0 Hz).

$^{13}$C NMR δ 135.2, 133.0, 132.8, 132.7, 132.2, 131.5 (q, J=3.1 Hz), 130.2 (q, 1=2.9 Hz), 129.9, 129.8, 128.3 (q, J=2.9 Hz), 124.3, 123.8 (q, J=285.7 Hz), 123.7 (q, J=285.7 Hz), 73.0 (q, J=28.0 Hz), 72.9 (q, J=28.0 Hz).

$^{19}$F NMR δ −79.34 (s, 3F), −79.40 (s, 3F).

IR (KBr) ν 3678, 3516, 3302, 3175, 2926, 2851, 2668, 2859, 1754, 1622, 1591, 1481, 1448, 1397, 1335, 1284, 1185, 940, 753, 637 cm$^{−1}$.

[Chem 19]

(d)

Example 2-b

Synthesis of Compound (e)

The same operations were performed except that the compound (b) in Example 1-c was changed to the compound (d) (2.015 g, 4.73 mmol) and stirring was conducted at room temperature over night. A crude product was purified by a column chromatography (developing solvent: hexane). The objective compound e (1.742 g, 94% yield) was obtained as a yellow solid.

(Analytical Results)

m.p. 79-80° C.

$^1$H NMR δ 8.69 (1H, t, J=1.7 Hz), 8.49 (2H, m), 8.38 (1H, dd, J=2.0, 9.8 Hz), 7.69 (1H, d, J=1.8 Hz), 7.64 (2H, dd, J=3.3, 6.9 Hz).

$^{19}$F NMR δ 49.82 (s, 3F), −49.98 (s, 3F).

IR (KBr) ν 3168, 3088, 3044, 2923, 2852, 2237, 1921, 1741, 1607, 1280, 1115, 957, 813, 702 cm$^{−1}$.

Anal. Calcd for $C_{24}H_{12}F_6$: C, 48.88; H, 1.79. Found: C, 48.48; H, 1.80.

[Chem 20]

(e)

Example 3-a

Synthesis of Compound (f)

The same operations were performed except that 2-bromoanthraquinone in Example 2-a was changed to 2-iodoanthraquinone (1.57 g, 4.68 mmol). The objective compound (f) (2.018 g, 91% yield) was obtained as a pale yellow solid.

(Analytical Results)

$^1$H NMR δ 8.39 (1H, t, J=2.1 Hz), 8.04-8.00 (2H, m), 7.91 (1H, dd, J=1.8, 8.4 Hz), 7.75 (1H, dq, J=2.2, 8.5 Hz), 7.56 (2H, dd, J=1.8, 6.0 Hz).

$^{13}$C NMR δ 138.4, 138.3, 137.4 (q, J=3.1 Hz), 135.4, 133.2, 133.0, 131.5 (q, J=290.0 Hz), 130.1 (q, J=2.9 Hz), 129.4, 129.4, 129.3, 129.3 (q, J=2.3 Hz, 2C), 123.9 (q, J=279.5 Hz), 73.6 (q, J=34.0 Hz), 73.5 (q, J=27.8 Hz).

$^{19}$F NMR δ −79.34 (s, 3F), −79.42 (s, 3F).

IR (KBr) ν 3677, 3514, 3317, 3193, 3083, 2821, 2366, 2359, 2352, 2112, 1956, 1932, 1709, 1621, 1585, 1478, 1219, 934, 714, 633 cm$^{−1}$.

[Chem 21]

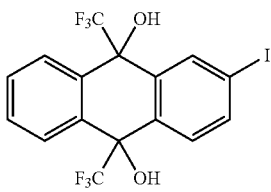

(f)

Example 3-b

Synthesis of Compound (g)

The same operations were performed except that the compound (b) in Example 1-c was changed to the compound (t) (2.018 g, 4.26 mmol) and stirring was conducted at room temperature over night. The objective compound (g) (1.114 g, 59% yield) was obtained as a yellow solid.

(Analytical Results)

$^1$H NMR δ 8.90 (1H, s), 8.49 (2H, dd, J=2.1, 5.4 Hz), 8.21 (1H, dd, J=1.8, 9.6 Hz), 7.81 (1H, dd, J=1.4, 9.8 Hz), 7.63 (2H, dd, J=3.3, 6.9 Hz).

$^{13}$C NMR δ 135.5, 133.3 (q, J=6.4 Hz), 133.3 (q, J=6.2 Hz), 130.0, 129.6, 129.3, 129.1 (q, J=233.7 Hz), 129.1 (q, J=234.9 Hz), 127.7, 127.5, 127.1, 126.2 (q, J=28.7 Hz), 124.6 (q, J=5.8 Hz), 124.6 (q, J=6.0 Hz), 123.4, 119.7.

$^{19}$F NMR δ −49.83 (s, 3F), −49.84 (s, 3F).

IR (KBr) ν 3164, 3158, 3146, 3139, 3117, 3087, 3064, 3050, 3033, 2369, 2352, 1925, 1600, 1523, 1492, 1461, 1434, 1378, 1342, 1281, 1120, 1051, 955, 764, 685, 625 cm$^{-1}$.

[Chem 22]

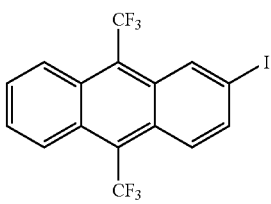

(g)

Example 4

Synthesis of Compound (h)

After a 50 mL two-neck flask was subjected to argon substitution, the compound (g) (0.318 g, 0.866 mmol), triethylamine (manufactured by Wako Pure Chemical Industries, Ltd., 15.4 mL), piperidine (manufactured by Wako Pure Chemical Industries, Ltd., 3.1 mL), phenylacetylene (manufactured by Tokyo Chemical Industry Co., Ltd., 0.11 mL, 1.0 mmol), bistriphenylphosphine palladium(II) dichloride (0.009 g, 1.5 mol %), and copper(I) iodide (0.002 g, 1.5 mol %) were added thereto, followed by heating at 80° C. for 2 hours and stirring at room temperature over night. After quenching with 1N hydrochloric acid, extraction was conducted with hexane and extract was dried over anhydrous magnesium sulfate and concentrated. A column chromatography was performed with a hexane solvent and the resulting solid was recrystallized from a hexane solvent. The objective compound (h) (0.1157 g, 32% yield) was obtained as a yellow solid.

(Analytical Results)

m.p. 110-112° C.

$^1$H NMR δ 8.69 (1H, t, J=2.1 Hz), 8.52-8.45 (3H, m), 7.69-7.61 (5H, m), 7.42-7.38 (3H, m).

$^{13}$C NMR δ 132.5, 131.4, 130.9, 130.9, 129.7, 129.7, 129.1, 128.8, 128.5 (q, J=41.9 Hz), 128.5 (q, J=41.3 Hz), 128.4, 128.4, 127.7 (q, J=5.7 Hz), 127.4, 127.4, 125.4 (q, J=275.4 Hz), 125.4 (q, J=275.6 Hz), 124.7 (q, J=5.8 Hz), 124.7 (q, J=5.7 Hz), 122.6, 122.4, 122.3, 92.4, 89.1.

$^{19}$F NMR δ −49.77 (s, 3F), −49.88 (s, 3F).

IR (KBr) ν 3432, 3142, 3129, 3087, 3065, 3053, 3042, 2930, 2925, 2364, 2347, 2335, 2218, 1960, 1615, 1495, 1434, 1364, 1288, 1027, 921, 852, 713, 644 cm$^{-1}$.

Anal. Calcd for $C_{24}H_{12}F_6$: C, 69.57; H, 2.92. Found: C, 69.48; H, 2.57.

UV: 207, 222, 280, 395 nm ($\lambda_{max}$=222 nm).

Fluorescence (absorption wavelength at 222 nm): 304, 330, 446, 462, 664 nm ($\lambda_{max}$=446 nm).

[Chem 23]

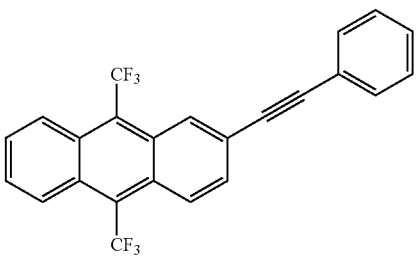

(h)

Example 5

Synthesis of Compound (i)

A 50 mL two-neck flask was subjected to argon substitution and the compound (g) (0.868 g, 1.97 mmol), 1,2-dimethoxyethane (manufactured by Tokyo Chemical Industry Co., Ltd., 10 mL) and tetrakis(triphenylphosphine)palladium(0) (manufactured by Wako Pure Chemical Industries, Ltd., 0.161 g, 1 mol %) were added thereto, followed by stirring for 20 minutes. Then, 6 mL of an aqueous sodium hydrogen carbonate solution and phenylboronic acid (manufactured by Tokyo Chemical Industry Co., Ltd., 0.268 g, 2.2 mmol) were added thereto, followed by refluxing for 14 hours. After quenching with water, extraction was conducted with dichloromethane, followed by washing with a 1N aqueous sodium hydroxide solution, drying over anhydrous sodium sulfate, and concentrating. A column chromatography was performed with a hexane solvent and the resulting solid was recrystallized from a hexane solvent. The objective compound (i) (0.5683 g, 74% yield) was obtained as a yellow solid.

(Analytical Results)

m.p. 105-106° C.

$^1$H NMR δ 8.69 (1H, t, J=2.0 Hz), 8.60 (1H, dd, J=2.1, 9.6 Hz), 8.51 (2H, m), 7.90 (1H, dd, J=1.7, 9.5 Hz), 7.78 (2H, dd, J=1.2, 8.4 Hz), 7.62 (2H, dd, J=3.6, 6.6 Hz), 7.55 (2H, dt, J=1.7, 6.6 Hz), 7.46-7.43 (1H, m).

$^{13}$C NMR δ 139.8, 139.8, 139.2, 139.2, 129.6 (q, J=1.6 Hz), 129.1, 128.4, 128.4, 128.3, 127.4, 127.2 (q, J=1.2 Hz), 127.0, 127.0, 125.7 (q, J=275.4 Hz), 125.7 (q, J=276.0 Hz), 125.6 (q, J=28.0 Hz), 125.6 (q, J=28.8 Hz), 125.5 (q, J=29.0 Hz), 125.2 (q, J=5.6 Hz), 124.6 (q, J=5.8 Hz), 124.5 (q, J=6.0 Hz), 121.9 (q, J=5.6 Hz).

$^{19}$F NMR δ −49.70 (s, 3F), −49.83 (s, 3F).

IR (KBr) ν 3447, 3065, 3037, 2957, 2923, 2852, 2361, 2352, 1920, 1631, 1581, 1525, 1493, 1466, 1492, 1381, 1290, 1186, 1110, 961, 884, 782, 731, 673, 638 cm$^{-1}$.

Anal. Calcd for $C_{22}H_{12}F_6$: C, 67.70; H, 3.10. Found: C, 67.83; H, 2.80.

UV: 413, 388, 282, 207 nm ($\lambda_{max}$=207 nm).

[Chem 24]

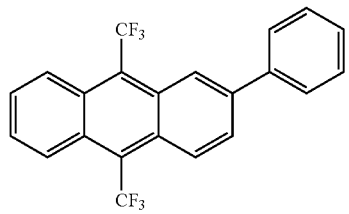

(i)

Example 6-a

Synthesis of Compound (j)

The same operations were performed except that anthraquinone in Example 1-a was changed to 2,6-dibromoanthraquinone (0.744 g, 2.04 mmol) and stirring was conducted at room temperature for 12 hours. The objective compound (j) (0.875 g, 85% yield) was obtained as a white solid.

(Analytical Results)

$^{1}$H NMR (CD$_3$CD) δ 8.36 (2H, dq, 3=2.1, 2.1 Hz), 7.93 (2H, dd, J=1.8, 8.7 Hz), 7.73 (2H, dq, J=8.4, 2.2 Hz).

$^{13}$C NMR (CD$_3$CD) δ 137.6, 133.4, 133.3, 132.5 (q, J=2.9 Hz), 131.6 (q, J=2.7 Hz), 125.6 (q, J=285.7 Hz) 73.7 (q, 3=27.5 Hz).

$^{19}$F NMR (CD$_3$CD) δ −77.55 (s).

[Chem 25]

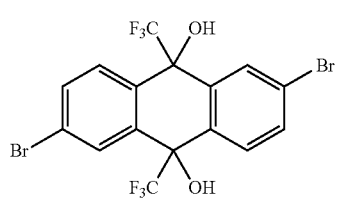

(j)

Example 6-b

Synthesis of Compound (k)

The same operations were performed except that the compound (b) in Example 1-c was changed to the compound (j) (2.14 g, 4.24 mmol) and stirring was conducted at room temperature over night. The objective compound (k) (1.52 g, 76% yield) was obtained as a yellow solid.

(Analytical Results)

$^{1}$H NMR δ 8.66 (2H, s), 8.36 (2H, d, J=9.6 Hz), 7.69 (2H, dd, 3=1.7, 9.8 Hz).

$^{19}$F NMR δ −50.00 (s).

[Chem 26]

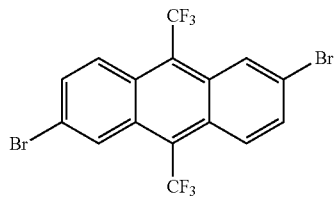

(k)

Example 6-c

Synthesis of Compound (1)

A 50 mL two-neck flask was subjected to argon substitution and the compound k (0.047 g, 0.1 mmol), toluene (manufactured by Wako Pure Chemical Industries, Ltd., 1.25 mL), water (0.625 mL), ethanol (0.31 mL), potassium carbonate (manufactured by Kanto Chemical Co., Inc., 0.163 g, 1.2 mmol), phenylboronic acid (manufactured by Tokyo Chemical Industry Co., Ltd., 0.026 g, 0.22 mmol), and tetrakis (triphenylphosphine) palladium(0) (manufactured by Wako Pure Chemical Industries, Ltd., 0.012 g, 10 mol %) were added thereto, followed by refluxing for 12 hours. After quenching with water, extraction was conducted with ethyl acetate, followed by washing with a 1N aqueous sodium hydroxide solution, drying over anhydrous sodium sulfate, and concentrating. A column chromatography was performed with a hexane solvent and the objective compound (1) (0.0291 g, 62% yield) was obtained as a yellow solid.

(Analytical Results)

m.p. 211-213° C.

$^{1}$H NMR δ 8.70 (2H, s), 8.61 (2H, d, J=9.6 Hz), 7.93 (2H, dt, J=2.0, 9.7 Hz), 7.79 (4H, dd, J=1.8, 7.2 Hz), 7.56 (4H, dt, J=2.3, 7.4 Hz), 7.48 (2H, dd, J=2.3, 7.4 Hz).

$^{19}$F NMR δ −49.75 (s).

IR (KBr) ν 3426, 3080, 3068, 3045, 3032, 2361, 1632, 1520, 1468, 1411, 1371, 1321, 1279, 1210, 1141, 1112, 962, 880, 821, 765 cm$^{-1}$.

Anal. Calcd for $C_{28}H_{16}F_6$: C, 72.10; H, 3.46. Found: C, 72.25; H, 3.18.

UV: 207, 221, 300, 406, 429 nm ($\lambda_{max}$=300 nm).

Fluorescence (absorption wavelength at 300 nm): 300, 460, 600 nm ($\lambda_{max}$=460 nm).

[Chem 27]

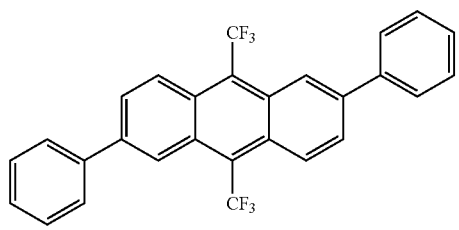

(l)

Example 7-a

Synthesis of Compound (m)

CF$_3$TMS (manufactured by Tosoh F-Tech, Inc., 0.85 mL, 5.7 mmol) was added to an N,N-dimethylformamide (manufactured by Wako Pure Chemical Industries, Ltd., 5 mL) solution of 6,13-pentaquinone (0.585 g, 1.9 mmol) and potassium carbonate (manufactured by Kanto Chemical Co., Inc., 0.240 g, 1.7 mmol) at 0° C., followed by stirring at room temperature for 15 hours. Thereafter, the reaction mixture was poured into a mixture of an aqueous saturated ammonium chloride solution (15 mL) and 1N HCl (5.0 mL), followed by extracting with diethyl ether. After the obtained organic layer was dried over anhydrous sodium sulfate, the organic solvents were removed by using a rotary evaporator. A crude product was purified by a column chromatography (manufactured by Kanto Chemical Co., Inc., silica gel 60 (spherical, 63-210 μm), developing solvent: hexane/dichloromethane=5:1). The objective compound (m) (0.498 g, 42% yield) was obtained as a white solid.
(Analytical Results)
m.p. 261-263° C.
$^1$H NMR δ –0.00 (s, 18H), 7.58-7.65 (m, 4H), 7.96-8.04 (m, 4H), 8.52 (d, 3=2.1 Hz, 411).
$^{13}$C NMR δ 1.9, 75.9 (q, J=27.9 Hz), 120.9 (q, J=287.2 Hz), 126.7, 128.2, 130.1 (q, J=2.5 Hz), 130.3, 132.7.
$^{19}$F NMR δ –80.27 (s).
IR (KBr) ν 3055, 2983, 2961, 2896, 1597, 1405, 1254, 1234, 1176, 1163, 1122, 1048, 992, 907, 843 cm$^{-1}$.

[Chem 28]

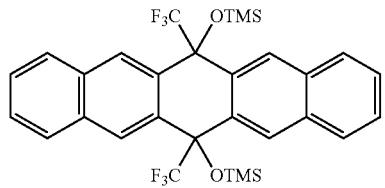

(m)

Example 7-b

Synthesis of Compound (n)

The compound (m) (0.593 g, 1.0 mmol) was dissolved in tetrahydrofuran (4.0 mL) and concentrated hydrochloric acid (0.3 mL, 3.6 mmol) was added thereto, followed by refluxing. After 3 hours, the reaction mixture was poured into an aqueous saturated ammonium chloride solution (20 mL) and a crude product was extracted with ethyl acetate. After the obtained organic layer was dried over anhydrous sodium sulfate, the solvents were removed by using a rotary evaporator. A crude product was purified by a column chromatography (developing solvent: hexane/ethyl acetate=2:1). The objective compound (n) (0.400 g, 89% yield) was obtained as a white solid.
(Analytical Results)
m.p.>300° C.
$^1$H NMR (CD$_3$OD) δ 4.88 (brs, 2H), 7.57-7.62 (m, 4H), 7.94-8.06 (m, 4H), 8.60 (d, 3=1.8 Hz, 4H).
$^{13}$C NMR (Acetone-d$_6$) δ 74.5 (q, J=27.2 Hz), 125.8 (q, J=286.5 Hz), 128.3, 129.1, 129.7 (q, J=2.5 Hz), 132.2, 134.0.
$^{19}$F NMR (CD$_3$OD) δ –77.96 (s).

IR (KBr) ν 3455, 3071, 1971, 1815, 1710, 1600, 1496, 1307, 1218, 1173, 1121, 1005, 869, 751 cm$^{-1}$.

[Chem 29]

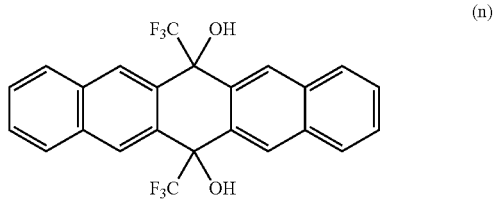

(n)

Example 7-c

Synthesis of Compound (o)

Triphenylphosphine (manufactured by Kanto Chemical Co., Inc., 0.367 g, 1.4 mmol) was added to a dichloromethane (manufactured by Kanto Chemical Co., Inc., 2.0 mL) solution of the compound (n) (0.134 g, 0.3 mmol) and carbon tetrabromide (manufactured by Tokyo Chemical Industry Co., Ltd., 0.298 g, 0.9 mmol) at 0° C., followed by refluxing for 2 hours. After 2 hours, the reaction mixture was poured into an aqueous saturated ammonium chloride solution (20 mL) and a crude product was extracted with dichloromethane. After the obtained organic layer was dried over anhydrous sodium sulfate, the solvent was removed by using a rotary evaporator. A crude product was purified by a column chromatography (developing solvent: hexantholuene=20:1). Then, recrystallization was conducted from hot methanol/chloroform=10:1 to obtain the objective compound (o) (0.025 g, 20% yield) as a dark blue solid.
(Analytical Results)
m.p. 209° C. (decomposition)
$^1$H NMR δ 7.38-7.48 (m, 4H), 7.91-7.97 (m, 4H), 9.10 (d, J=1.2 Hz, 4H).
$^{19}$F NMR δ –49.59 (s). IR (KBr) ν 3057, 2925, 2855, 1359, 1219, 1179, 1161, 1108, 869, 738 cm$^{-1}$.
HRMS (FAB). found: m/z 414.0835. Calcd for C$_{24}$H$_{12}$F$_5$ (M$^+$): 414.0843.

[Chem 30]

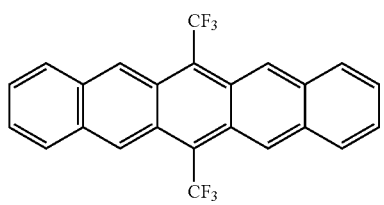

(o)

Example 8-a

Synthesis of Compound (p)

The same operations were performed except that 6,13-pentaquinone in Example 7-a was changed to 5,7,12,14-tetrahydropentacene-5,7,12,14-tetraone (0.0788 g, 0.23 mmol) to obtain the objective compound (p) (0.0328 g, 16% yield) as a white solid.

(Analytical Results)

$^1$H NMR δ 0.09 (18H, s), 7.26-7.56 (2H, m), 7.98-8.01 (2H, m), 8.62 (1H, s). $^{13}$C NMR δ 75.8 (q, J=28.2 Hz), 125.7 (q, J=288.1 Hz), 130.8, 131.3 (q, J=3.3 Hz), 131.6 (sept, J=3.3 Hz), 133.3, 136.5.

$^{19}$F NMR δ −78.11 (s).

IR (KBr) ν 2969, 1487, 1450, 1410, 1255, 1121, 987, 960, 910, 761, 728, 685, 657, 630 cm$^{-1}$.

Anal. Calcd for $C_{38}H_{46}F_{12}O_4Si_4$: C, 50.32; H, 5.11. Found: C, 50.16; H, 5.57.

[Chem 31]

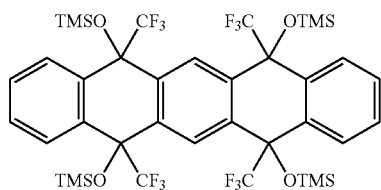

(p)

Example 8-b

Synthesis of Compound (q)

The same operations were performed except that the compound (n) in Example 7-b was changed to the compound (p) (0.075 g, 0.083 mmol) to obtain the objective compound (q) (0.045 g, 89% yield) was obtained as a white solid.

(Analytical Results)

$^1$H NMR δ 2.82 (4H, s), 7.62-7.67 (214, m), 8.12 (2H, s), 8.83 (1H, s).

$^{13}$C NMR δ 73.9 (q, J=27.6 Hz), 126.0 (q, J=287.8 Hz), 129.7, 129.9, 130.83 (sept, 3=3.1 Hz), 135.5, 136.6.

$^{19}$F NMR δ −76.68 (s).

IR (KBr) ν 3629, 3420, 3137, 2956, 1491, 1416, 1354, 1229, 1176, 1120, 1052, 985, 920, 897, 776, 744, 689, 646, 629 cm$^{-1}$.

[Chem 32]

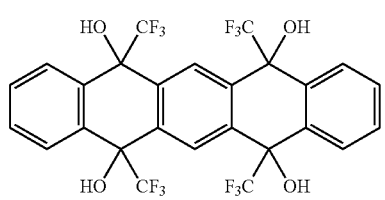

(q)

Example 8-c

Synthesis of Compound (r)

The same operations were performed except that the compound (n) in Example 7-c was changed to the compound (q) (0.040 g, 0.064 mmol) to obtain the objective compound (r) (0.051 g, 14% yield) as a bluish purple solid.

(Analytical Results)

$^1$H NMR δ 7.52-7.56 (4H, m), 8.44 (4H, s), 9.96 (2H, s).

$^{19}$F NMR δ −50.27 (s).

HRMS (FAB). found: m/z 550.0546. Calcd for $C_{26}H_{10}F_{12}$ (M$^+$): 550.0591.

[Chem 33]

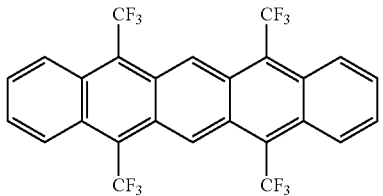

(r)

Example 9

Synthesis of Compound (s)

The same operations were performed except that phenylboronic acid in Example 5 was changed to 4-methoxyphenylboronic acid (0.082 g, 0.60 mmol) to obtain the objective compound (s) (0.167 g, 80% yield) as a yellow solid.

(Analytical Results)

$^1$H NMR δ 7.61 (2H, m), 7.727 (1H, q, 3=5.0 Hz), 7.728 (1H, d, 3=8.7 Hz), 7.89 (1H, dd, J=2.1, 9.6 Hz), 8.50 (2H, dquint, J=7.6, 2.5 Hz), 8.57 (1H, ddq, 3=0.6, 9.6, 2.3 Hz), 8.62 (1H, quint, 3=2.0 Hz).

$^{13}$C NMR δ 55.3, 114.5, 120.7 (q, J=5.6 Hz), 124.5 (q, 3=5.6 Hz), 124.6 (q, 3=5.6 Hz), 125.1 (q, 3=5.6 Hz), 125.2 (q, J=26.3 Hz), 125.5 (q, 3=26.7 Hz), 125.6 (q, 3=275.8 Hz), 126.9, 125.7 (q, J=125.7 Hz), 127.07, 127.10, 128.20, 128.22, 128.8, 128.9, 129.6, 128.7, 132.1, 138.7, 159.9.

$^{19}$F NMR δ −49.88 (s), −49.82 (s).

IR (KBr) ν 3434, 3132, 3046, 3005, 2964, 2936, 2898, 2837, 2784, 2550, 2360, 2058, 1609, 1578, 1522, 1496, 1467, 1252, 1187, 1115, 959, 812, 718, 643 cm$^4$.

Anal. Calcd for $C_{23}H_{14}F_6O$: C, 65.72; H, 3.36. Found: C, 65.46; H, 3.10.

[Chem 34]

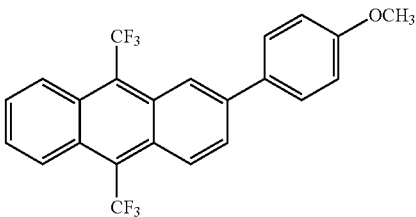

(s)

Example 10

Synthesis of Compound (t)

The same operations were performed except that phenylboronic acid in Example 5 was changed to 4-trifluoromethylphenylboronic acid (0.021 g, 0.11 mmol) to obtain the objective compound (t) (0.041 g, 90% yield) as a yellow solid.

(Analytical Results)

m.p. 114.5-116.0° C.

$^1$H NMR δ 7.65 (2H, dd, J=3.3, 7.2 Hz), 7.80 (2H, d, J=7.8 Hz), 7.89 (3H, m), 8.53 (2H, m), 8.64 (1H, ddq, J=0.4, 9.4, 2.0 Hz), 8.70 (1H, quint, J=2.1 Hz).

$^{13}$C NMR δ 124.1 (q, J=270.0 Hz), 124.6 (q, 1=5.9 Hz), 124.7 (q, 3=5.9 Hz), 125.5 (q, 3=275.8 Hz), 125.6 (q, J=275.8

Hz), 125.6 (q, 1=5.6 Hz), 126.0 (q, J=4.4 Hz), 126.6, 127.4, 127.5, 127.7, 124.8, 128.5, 129.2, 129.3, 123.36, 129.39, 129.68, 129.71, 139.3 (q, 3=32.3 Hz), 137.7, 143.3.

$^{19}$F NMR δ −63.85 (s, 3F), −49.89 (s, 3F), −49.68 (s, 3F).

IR (KBr) ν 3416, 3139, 3056, 2930, 2823, 2851, 2646, 2360, 1970, 1924, 1799, 1726, 1677, 1630, 1617, 1580, 1557, 1529, 1496, 1440, 1383, 1174, 1135, 1074, 1053, 961, 817, 728, 678, 624 cm$^{-1}$.

Anal. Calcd for $C_{23}H_{11}F_9$: C, 60.27; H, 2.42. Found: C, 60.10; H, 2.36.

[Chem 35]

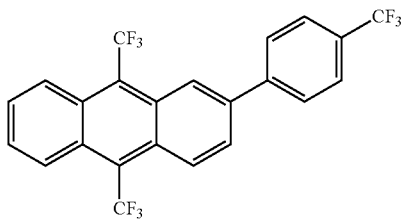

(t)

Example 11

Synthesis of Compound (u)

The same operations were performed except that phenylboronic acid in Example 5 was changed to thiophene-2-boronic acid (0.077 g, 0.60 mmol) to obtain the objective compound (u) (0.200 g, 99% yield) as a yellow solid.

(Analytical Results)

m.p. 137-138° C.

$^1$H NMR δ 7.18 (1H, dd, 3=3.6, 5.1 Hz), 7.43 (1H, dd, J=0.9, 5.1 Hz), 7.61 (1H, dd, J=2.9, 4.1 Hz), 7.61 (1H, dd, J=0.8, 10.4 Hz), 7.89 (1H, dd, J=2.1, 9.6 Hz), 8.52 (3H, m), 8.69 (1H, quint, 3=2.1 Hz).

$^{13}$C NMR δ 119.7 (q, 3=5.8 Hz), 124.5 (q, J=5.6 Hz), 124.7 (q, 3=5.6 Hz), 125.3 (q, 3=5.8 Hz), 125.5 (q, J=276.2 Hz), 125.6 (q, 3=276.1 Hz), 125.7 (q, 1=27.7 Hz), 126.0, 126.6, 127.0, 127.3, 127.4, 128.5, 128.97, 128.99, 129.46, 129.48, 129.8, 132.6, 143.1.

$^{19}$F NMR δ −49.87 (s, 3F), −49.92 (s, 3F).

IR (KBr) ν 3154, 3155, 3080, 3048, 2924, 2849, 1968, 1920, 1836, 1800, 1772, 1742, 1720, 1631, 1616, 1559, 1532, 1517, 1501, 1474, 1438, 1350, 1285, 1192, 1169, 952, 763, 687, 633 cm$^{-1}$.

Anal. Calcd for $C_{20}H_{10}F_6S$: C, 60.61; H, 2.52. Found: C, 60.22; H, 2.27.

[Chem. 36]

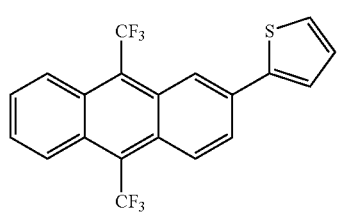

(u)

Example 12-a

Synthesis of Compound (v)

The same operations were performed except that anthraquinone in Example 1-a was changed to 2,6-diiodoanthraquinone (0.8578 g, 1.867 mmol) and stirring was conducted at room temperature for 12 hours. The objective compound (v) (0.2825 g, 25% yield) was obtained as a white solid.

(Analytical Results) NMR (CD$_3$OD) δ 8.31 (2H, dq, J=2.1, 2.1 Hz), 7.91 (1H, dd, J=2.1, 8.7 Hz), 7.72 (2H, dq, J=8.4, 2.2 Hz).

$^{13}$C NMR (CD$_3$OD) δ 139.2, 138.7 (q, J=2.8 Hz), 137.3, 134.9, 131.4 (q, J=2.5 Hz), 125.2 (q, J=286.1 Hz), 95.9, 73.6 (q, J=27.3 Hz).

$^{19}$F NMR (CD$_3$OD) δ −79.56 (s, 3F).

[Chem 37]

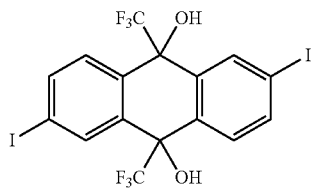

(v)

Example 12-b

Synthesis of Compound (w)

The same operations were performed except that the compound (b) in Example 1-c was changed to the compound (v) (0.2825 g, 0.471 mmol) and stirring was conducted at room temperature over night. The objective compound w (0.2100 g, 79% yield) was obtained as a yellow solid.

(Analytical Results)

$^1$H NMR δ 8.66 (2H, s), 8.36 (2H, d, J=9.6 Hz), 7.69 (2H, dd, J=1.7, 9.8 Hz).

$^{19}$F NMR δ −50.00 (s).

Anal. Calcd for $C_{16}H_6F_6I_2$: C, 33.35; H, 1.07. Found: C, 33.91; H, 1.00.

[Chem 38]

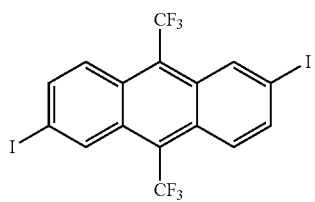

(w)

Example 13-a

Synthesis of Compound (x)

The same operations were performed except that the compound (k) in Example 6-c was changed to the compound (w) (0.045 g, 0.08 mmol) and phenylboronic acid was changed to 4-methoxyphenylboronic acid (0.022 g, 0.18 mmol) to obtain the objective compound (x) (0.030 g, 85% yield) as a yellow solid.

(Analytical Results)

$^1$H NMR δ 8.62 (2H, s), 8.57 (2H, d, J=9.3 Hz), 7.89 (2H, d, J=9.6 Hz), 7.73 (4H, d, J=8.7 Hz), 7.08 (4H, d, J=8.7 Hz), 3.90 (6H, s).

$^{19}$F NMR δ −49.86 (s).

HRMS (FAB). found: m/z 526.1336. Calcd for $C_{30}H_{20}F_6O_2$ (M$^+$): 526.1367.

[Chem 39]

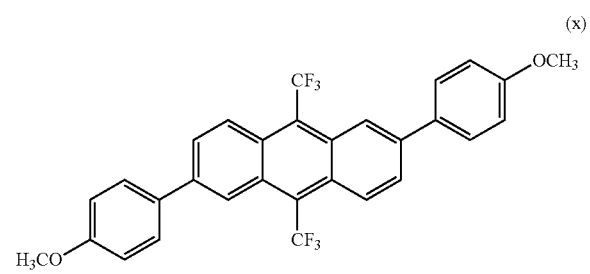

Example 13-b

Synthesis of Compound (y)

The same operations were performed except that the compound (k) in Example 6-c was changed to the compound (w) (0.082 g, 0.6 mmol) and phenylboronic acid was changed to 4-trifluoromethylphenylboronic acid (0.021 g, 0.11 mmol) to obtain the objective compound (y) (0.025 g, 90% yield) as a yellow solid.

(Analytical Results)

m.p. 216.8-218.0° C.

$^1$H NMR δ 8.72 (2H, s), 8.68 (2H, d, J=8.4 Hz), 7.92 (2H, dd, J=1.5, 9.1 Hz), 7.89 (4H, d, J=8.1 Hz), 7.81 (4H, d, J=8.1 Hz).

$^{19}$F NMR δ −63.86 (s, 6F), −49.70 (s, 6F).

IR (KBr) ν 3428, 3127, 3047, 2934, 2850, 2643, 1928, 1803, 1781, 1630, 1399, 1209, 1073, 847, 768, 698, 605 cm$^{-1}$.

Anal. Calcd for $C_{30}H_{14}F_{12}$: C, 58.81; H, 2.34. Found: C, 59.51; H, 2.14.

[Chem. 40]

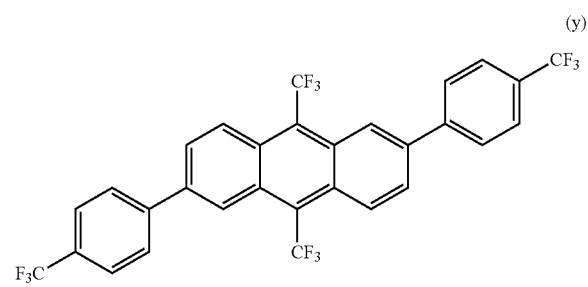

Example 14

Synthesis of Compound (a1)

A 50 mL two-neck flask was subjected to argon substitution and the compound (g) (0.132 g, 0.3 mmol) synthesized in Example 3-b, DMF (3 mL), Pd(PPh$_3$)$_2$Cl$_2$ (0.010 g, 0.015 mmol, 5 mol %), CuI (0.003 g, 0.015 mmol, 5 mol %), Et$_3$N (0.17 mL, 1.2 mmol), and 4-(methoxyphenyl)acetylene (0.042 g, 0.32 mmol) were successively put therein, followed by stirring at room temperature for 4 hours. After quenching with an aqueous saturated ammonium chloride solution, extraction was conducted with 15 mL of diethyl ether three times and extract was dried over MgSO$_4$ and concentrated. A column chromatography was performed with a hexane: dichloromethane=4:1 solvent and the resulting solid was recrystallized from a hexane solvent to isolate the objective compound (a1) (2-[(4-methoxyphenyl)ethynyl]-9,10-bis(trifluoromethyl)anthracene) as a yellow solid (0.106 g, 0.239 mmol, yield: 80%).

(Analytical Results)

$^1$H NMR (300 MHz, CDCl$_3$) δ 8.65 (1H, t, J=1.8 Hz), 8.48 (3H, m), 7.61 (5H, m), 6.93 (2H, m), 3.86 (3H, s).

$^{19}$F NMR (283 MHz, CDCl$_3$) δ −49.87 (s, 3F), −49.93 (s, 3F).

$^{13}$C NMR (75 MHz, CDCl$_3$) δ 160.0, 133.4, 129.63, 129.61, 129.4, 129.31, 129.29, 128.82, 128.80, 128.11, 128.09, 127.42 (q, J=278.1 Hz), 127.37, 127.2 (q, J=5.6 Hz), 125.7 (q, J=28.6 Hz), 125.4 (q, J=275.8 Hz), 125.0 (q, J=28.4 Hz), 124.64 (q, J=5.2 Hz), 124.57 (q, J=5.4 Hz), 122.7, 114.6, 114.1, 92.6, 88.1, 55.2.

Rf=0.29 (Hexane:CH$_2$Cl$_2$=4:1)

IR (KBr) ν 3172, 3124, 3096, 3050, 3018, 2974, 2950, 2938, 2911, 2896, 2840, 2812, 2549, 2217, 2042, 1968, 1921, 1899, 1838, 1770, 1722, 1569, 1556, 1435, 1320, 955, 914, 784, 647 cm$^{-1}$.

mp 123.5-124.1° C.

Anal. Calcd for $C_{25}H_{14}F_6O$: C, 67.57; H, 3.18. Found: C, 67.50; H, 3.35.

[Chem. 41]

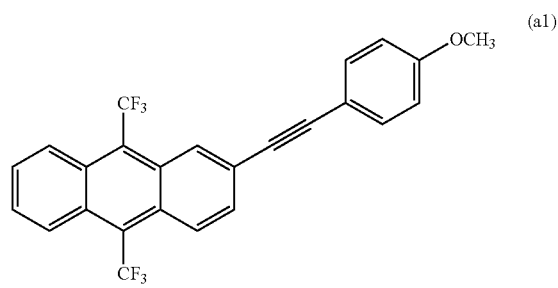

Example 15

Synthesis of Compound (b1)

A 50 mL two-neck flask was subjected to argon substitution and the compound (w) (0.028 g, 0.05 mmol) obtained in Example 12-b, Pd(PPh$_3$)$_2$Cl$_2$ (0.002 g, 0.0025 mmol, 5 mol %), CuI (0.001 g, 0.005 mmol, 10 mol %), PPh$_3$ (0.001 g, 0.005 mmol, 10 mol %), Et$_3$N (0.25 mL, 1.79 mmol), CH$_3$Ph (0.3 mL), and phenylacetylene (0.122 g, 0.12 mmol) were successively put therein, followed by stirring at room temperature for 6.5 hours. After quenching with an aqueous saturated ammonium chloride solution, extraction was conducted with 15 mL of ethyl acetate three times and extract was dried over MgSO$_4$ and concentrated. A column chromatography was performed with a hexane solvent and the resulting solid was recrystallized from a hexane solvent to isolate the objective compound (b1) (2,6-bis(phenylethynyl)-9,10-bis(trifluoromethyl)anthracene) as a yellow solid (0.022 g, 0.432 mmol, yield: 86%).

(Analytical Results)

$^1$H NMR (300 MHz, CDCl$_3$) δ 8.67 (2H, s), 8.48 (2H, d, J=8.7 Hz), 7.67 (6H, m), 7.41 (6H, quint, J=3.2 Hz).

$^{19}$F NMR (283 MHz, CDCl$_3$) δ −46.20 (s).

$^{13}$C NMR (75 MHz, CDCl$_3$) δ 131.9, 129.7, 129.0, 128.9, 128.7, 128.5, 127.7 (q, J=6.0 Hz), 125.3 (q, J=29.0 Hz), 125.2 (q, J=304.6 Hz), 124.8 (q, J=5.8 Hz), 122.7, 122.5, 92.7, 89.1

Rf=0.57 (Hexane:CH$_2$Cl$_2$=4:1)

IR (KBr) ν 3437, 3148, 3100, 3082, 3054, 3032, 3019, 2995, 2210, 1625, 1496, 1442, 1413, 1365, 1326, 1285, 1172, 994, 923, 881, 811, 720, 687, 659, 580, 542, 526, 480, 422

Anal. Calcd for C$_{32}$H$_{16}$F$_6$: C, 74.71; H, 3.13. Found: C, 74.67; H, 2.96.

mp 215.0-215.5° C.

[Chem. 42]

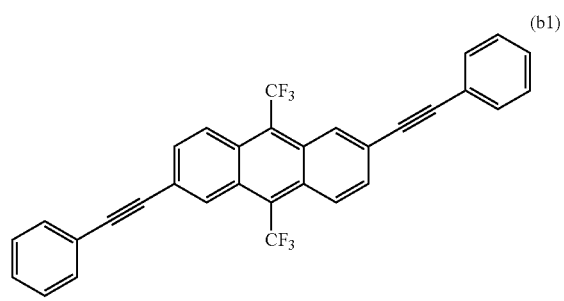

(b1)

Example 16

Synthesis of Compound (c1)

A 50 mL two-neck flask was subjected to argon substitution and the compound (w) (0.028 g, 0.05 mmol) obtained in Example 12-b, Pd(PPh$_3$)$_2$Cl$_2$ (0.002 g, 0.0025 mmol, 5 mol %), CuI (0.001 g, 0.005 mmol, 10 mol %), PPh$_3$ (0.001 g, 0.005 mmol, 10 mol %), Et$_3$N (1 mL, 7.17 mmol), CH$_3$Ph (0.3 mL), and 4-methoxyphenylacetylene (0.016 g, 0.12 mmol) were successively put therein, followed by stirring at room temperature for 2 hours. After quenching with an aqueous saturated ammonium chloride solution, extraction was conducted with 15 mL of ethyl acetate three times and extract was dried over MgSO$_4$ and concentrated. A column chromatography was performed with a hexane: dichloromethane=1:1 solvent and the resulting solid was recrystallized from a hexane solvent to isolate the objective compound (c1) (2,6-bis(4-methoxyphenylethynyl)-9,10-bis(trifluoromethyl)anthracene) as a yellow solid (0.0165 g, 0.0287 mmol, yield: 57%).

(Analytical Results)

$^1$H NMR (300 MHz, CDCl$_3$) δ 8.63 (2H, m), 8.45 (2H, m), 7.67 (2H, m), 7.57 (4H, d, J=11.4 Hz), 6.93 (4H, d, J=8.7 Hz), 3.86 (6H, s).

$^{19}$F NMR (283 MHz, CDCl$_3$) δ −49.00 (s).

IR (KBr) ν 3807, 3122, 3076, 3043, 3028, 3006, 2962, 2946, 2849, 2545, 2207, 1626, 1604, 1568, 1514, 1465, 1444, 1367, 1325, 1285, 1252, 1171, 1030, 1010, 925, 840, 796, 729, 648, 574, 546, 485, 413 cm$^{-1}$.

mp 215.0-216.2

[Chem 43]

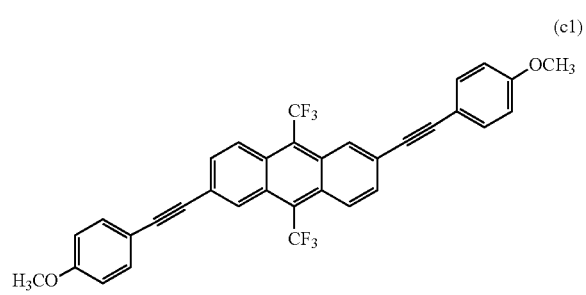

(c1)

Example 17

Synthesis of Compound (d1)

A 50 mL two-neck flask was subjected to argon substitution and the compound (w) (0.100 g, 0.177 mmol) obtained in Example 12-b, THF (2 mL), toluene (2 mL), 2-thienylboronic acid (0.067 g, 0.531 mmol), Na$_2$CO$_3$ aq (0.4 mL, 2M), and Pd(PPh$_3$)$_4$ (0.020 g, 0.0177 mmol, 10 mol %) were successively added thereto, followed by refluxing for 7 hours. After quenching with an aqueous saturated ammonium chloride solution, extraction was conducted with 15 mL of ethyl acetate three times and extract was dried over MgSO$_4$ and concentrated. A column chromatography was performed with a hexane: dichloromethane=4:1 solvent to isolate the objective compound (d1) (2,6-dithienyl-9,10-bis(trifluoromethyl) anthracene) (0.069 g, 0.144 mmol, yield: 82%).

(Analytical Results)

$^1$H NMR (300 MHz, CDCl$_3$) δ 8.68 (2H, s), 8.52 (2H, dd, J=1.2, 9.6 Hz), 7.90 (2H, dd, J=1.8, 9.3 Hz), 7.57 (2H, dd, J=0.9, 3.6 Hz), 7.43 (2H, dd, J=0.9, 8.1 Hz), 7.19 (2H, dd, J=3.6, 5.1 Hz).

$^{19}$F NMR (283 MHz, CDCl$_3$) δ −49.93 (s).

$^{13}$C NMR (75 MHz, CDCl$_3$) δ 143.2, 132.6, 129.2 (q, J=20.3 Hz), 128.5, 126.6, 126.3, 125.6 (q, J=280.5 Hz), 125.3 (q, J=3.3 Hz), 124.9, 119.9 (q, J=5.8 Hz).

IR (KBr) ν 3141, 3109, 3094, 3085, 2359, 2329, 1921, 1810, 1735, 1632, 1530, 1481, 1431, 1356, 1317, 1281, 1248, 1213, 1168, 1109, 1038, 948, 909. 867, 850, 831, 809, 777, 748, 703, 673, 648, 619, 598, 544, 490.

mp 241.8-242.3° C.

[Chem 44]

(d1)

Example 18-a

Synthesis of Compound (e1)

C$_2$F$_5$TMS (manufactured by Alfa Aesar Company, 0.423 g, 2.2 mmol) was added to an N,N-dimethylformamide (manufactured by Wako Pure Chemical Industries, Ltd., 10 mL) solution of 6,13-pentaquinone (0.308 g, 1.0 mmol) and potassium carbonate (manufactured by Kanto Chemical Co., Inc., 0.055 g, 0.4 mmol) at 0° C., followed by stirring at room temperature for 3 hours. Thereafter, the reaction mixture was poured into a mixture of an aqueous saturated ammonium chloride solution (15 mL) and 1N HCl (5.0 mL), followed by extracting with diethyl ether. After the obtained organic layer was dried over anhydrous sodium sulfate, the organic solvents were removed by using a rotary evaporator. A crude product was purified by a column chromatography (manufactured by Kanto Chemical Co., Inc., silica gel 60 (spherical, 63-210 μm), developing solvent: hexane). The objective compound (e1) (0.215 g, 31% yield) was obtained as a white solid.

(Analytical Results)

$^1$H NMR δ 0.17 (s, 18H), 7.60-7.64 (m, 4H), 7.97-8.01 (m, 4H), 8.49 (s, 4H).

$^{13}$C NMR δ 2.1, 77.9 (t, J=21.6 Hz), 113.8 (tq, J=268.0, 32.9 Hz), 119.2 (qt, J=289.0, 37.3 Hz), 127.5, 128.2, 129.7, 130.2, 132.5.

$^{19}$F NMR δ −77.30 (s, 6F), −119.19 (s, 4F).

[Chem 45]

(e1)

Example 18-b

Synthesis of Compound (f1)

The compound (e1) (0.215 g, 0.31 mmol) was dissolved in ethanol (4.0 mL) and concentrated hydrochloric acid (0.4 mL, 4.8 mmol) was added thereto, followed by refluxing. After 3 hours, the reaction mixture was poured into an aqueous saturated ammonium chloride solution (20 mL) and a crude product was extracted with ethyl acetate. After the obtained organic layer was dried over anhydrous sodium sulfate, the solvents were removed by using a rotary evaporator. A crude product was purified by a column chromatography (developing solvent: hexane/ethyl acetate=2:1). The objective compound (f1) (0.168 g, 99% yield) was obtained as a white solid.

(Analytical Results)

m.p. 272-274° C.

$^1$H NMR δ 3.30 (brs, 2H), 7.60-7.66 (m, 4H), 7.97-8.04 (m, 4H), 8.61 (s, 4H).

$^{19}$F NMR δ −79.55 (s, 6F), −124.09 (s, 4F).

IR (KBr) ν 3585, 3060, 1497, 1340, 1217, 1143, 990, 848, 750 cm$^{-1}$.

[Chem 46]

(f1)

Example 18-c

Synthesis of Compound (g1)

Triphenylphosphine (manufactured by Kanto Chemical Co., Inc., 0.354 g, 1.35 mmol) was added to a dichloromethane (manufactured by Kanto Chemical Co., Inc., 5.0 mL) solution of the compound (f1) (0.180 g, 0.32 mmol) and carbon tetrabromide (manufactured by Tokyo Chemical Industry Co., Ltd., 0.298 g, 0.9 mmol) at 0° C., followed by stirring at room temperature for 1 hour. After 1 hour, carbon tetrabromide (manufactured by Tokyo Chemical Industry Co., Ltd., 0.298 g, 0.9 mmol) and triphenylphosphine (manufactured by Kanto Chemical Co., Inc., 0.354 g, 1.35 mmol) were again added thereto, followed by stirring for another 1 hour. Thereafter, the reaction mixture was poured into an aqueous saturated ammonium chloride solution (20 mL) and a crude product was extracted with dichloromethane. After the obtained organic layer was dried over anhydrous sodium sulfate, the solvent was removed by using a rotary evaporator. A crude product was purified by a column chromatography (developing solvent: hexane). Then, recrystallization was conducted from hot methanol/chloroform=10:1 to obtain the objective compound (g1) (0.078 g, 47% yield) as a dark blue solid.

(Analytical Results)

m.p. 212° C. (decomposition).

$^1$H NMR δ 7.43-7.48 (m, 4H), 7.91-7.98 (m, 4H), 9.06 (brs, 4H).

$^{19}$F NMR δ −81.50 (s, 6F), −95.99 (s, 4F).

IR (KBr) ν 3066, 1311, 1220, 1172, 1041, 1013, 885, 737 cm$^{-1}$.

[Chem 47]

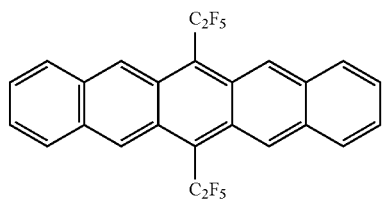

(g1)

<Method for Quantitative Determination Test 1 of Heavy Metal Content in Compound>

The compound (o) obtained in Example 7-c was subjected to a contamination analysis test of various heavy metal elements after sublimation purification.

A sample 5 mg was weighed in a platinum crucible and was converted into ashes by means of a gas burner. Then, 0.2 mL of sulfuric acid was charged thereinto and, after evaporation to dryness on a hot plate, temperature was raised to perform a white smoke treatment. A residue was dissolved with a hydrochloric acid solution and various elements (Cr, Mn, Fe, Co, Ni, Cu, Zn, Pb, P) were quantitatively determined by ICP-MS method. As an apparatus, quadrupole ICP-MS (ELAN-DRCII manufactured by PerkinElmer Co., Ltd.) was used. For quantitative determination of P, dipole ICP-MS (ELEMENT2 manufactured by Thermo Fisher Scientific K.K.) was used.

Results are shown in Table 1.

TABLE 1

Quantitative Determination Test 1
of Metal Content ($\mu g/g$)

| Element | Compound (o) |
|---|---|
| Cr | 2 |
| Mn | <1 |
| Fe | 16 |
| Co | <1 |
| Ni | <1 |
| Cu | <1 |
| Zn | <1 |
| Pb | <1 |
| P | <1 |

<Method for Quantitative Determination Test 2 of Halogen Content in Compound>

The compound (o) obtained in the above was subjected to a contamination analysis test of Br and Cl elements after sublimation purification.

A sample 5 mg was converted into a solution through a pre-treatment by an oxygen combustion flask method, and Cl and Br were quantitatively determined by an ion chromatography.

Contents of Br and Cl elements in the sample were shown in Table 2.

TABLE 2

Quantitative Determination Test 2
of Metal Content (wt %)

| Element | Compound (o) |
|---|---|
| Br | 1.4 |
| Cl | 0.5 |

From Table 1 and Table 2, it is realized that the fluorine-containing aromatic compounds synthesized by the manufacturing method of the present invention have a very small content of metal impurities. In comparison with the heavy metal content of commercially available organic semiconductors (about 25 ppm by mass), the content of heavy metals proves to be markedly low.

<Solubility Test of Compound>

In order to investigate applicability of the compound (o) obtained in Example 7-c to a wet process, a solubility test of the compound in various solvents was conducted. In addition, a solubility test of pentacene was also conducted as reference.

Specifically, 20 mg of a sample was weighed and it was visually judged whether it dissolves in 10 g of a solvent at room temperature (0.2% by weight).

Results are shown in Table 3.

TABLE 3

| | Solvent | Hexane | Cyclohexane | Toluene | THF | Chloroform | o-Dichlorobenzene |
|---|---|---|---|---|---|---|---|
| Ex. | Compound (o) | Yes | Yes | Yes | Yes | Yes | Yes |
| Comp. Ex. | Pentacene | No | No | No | No | No | No |

In Table 3, "Yes" represents "soluble" and "No" represents "insoluble".

As a result of the solubility test, it was revealed that the compounds synthesized in the present invention have a high solubility in organic solvents as compared with pentacene. Particularly, it was realized that the compounds are soluble even in low polar solvents such as hexane and cyclohexane.

<Property Evaluation of Deposition-Type Organic Semiconductor Material>

(1) Compound (o)

A cleaned silicon substrate was immersed in a toluene solution of n-octyltrichlorosilane to treat surface of the silicon oxide film. An organic semiconductor layer was formed by vacuum deposition of the compound (o) obtained in Example 7-c onto the substrate (back pressure: up to 104 Pa, deposition rate: 0.1 Å/s, substrate temperature: 25° C., film thickness: 70 nm).

Gold was vacuum-deposited on an upper part of the organic semiconductor layer (back pressure: up to $10^{-4}$ Pa, deposition rate: 1 to 2 Å/s, film thickness: 50 nm) by using a shadow mask to form source and drain electrodes (channel length: 50 μm, channel width: 1 mm). The organic semiconductor layer and the silicon oxide film existing at a site different from the electrodes were scraped away, and a conductive paste (DOTITE D-550 manufactured by Fujikura Kasei Co., Ltd.) was attached thereto and a solvent was dried. Thus, a field effect transistor (FET) element having a top-contact bottom-gate structure was prepared.

Using the part as a gate electrode, voltage was imparted to the silicon substrate. Electrical properties of the obtained FET (field effect transistor) element were evaluated under vacuum ($<5\times10^{-3}$ Pa) by using a semiconductor device analyzer B1500A manufactured by Agilent Company. As a result, the element exhibited properties as an n-type transistor element. Field effect mobility was determined from a saturated region in current-voltage properties of the organic thin-film transistor. The carrier mobility was $2.1\times10^{-3}$ cm$^2$/V·s.

(2) Compound (r)

By the same method as above, a field effect transistor (FET) element having a top-contact bottom-gate structure was prepared from the compound (r) obtained in Example 8-c. As a result of evaluation of electrical properties, the element exhibited properties as an n-type transistor element. Field effect mobility was determined from a saturated region in current-voltage properties of the organic thin-film transistor. The carrier mobility was $4.5 \times 10^{-6}$ cm$^2$/V·s.

<Thin Film X-Ray Diffraction>

Measurement of Out-of-plane X-ray diffraction pattern (diffraction caused by a lattice plane parallel to the substrate surface) was conducted for the deposition thin film of the compound (o) of Example 7-c which had been prepared in the above property evaluation. The measurement of Out-of-plane X-ray diffraction was evaluated by grazing incidence measurement using TTR-III manufactured by Rigaku Corporation, and diffraction lines corresponding to (110), (200) planes were observed.

Moreover, measurement of In-plane X-ray diffraction pattern (diffraction caused by a lattice plane perpendicular to the substrate surface) was conducted for the same deposition thin film. The measurement of In-plane X-ray diffraction was evaluated by using ATX-G manufactured by Rigaku Corporation and diffraction lines corresponding to d=4.5 Å were observed, so that it was realized that the compound has crystallinity in the thin film.

<Property Evaluation of Coating-Type Organic Semiconductor Material>

For property evaluation of a compound as a coating-type organic semiconductor material, a field effect transistor (coating FET) element was prepared by using a spin coating method and field effect mobility (carrier mobility) was determined. The following shows a method for preparing the coating FET element and an evaluation method of semiconductor properties.

A cleaned silicon substrate having a silicon oxide film was immersed in a toluene solution of n-octyltrichlorosilane to treat surface of the silicon oxide film. An organic semiconductor layer was formed by spin-coating a xylene solution (concentration: 0.4% by weight) of the compound (o) obtained in Example 7-c onto the above substrate.

Gold was vacuum-deposited on an upper part of the organic semiconductor layer (back pressure: up to $10^{-4}$ Pa, deposition rate: 1 to 2 Å/s, film thickness: 50 nm) by using a shadow mask to form source and drain electrodes (channel length: 50 μm, channel width: 1 mm). The organic semiconductor layer and the silicon oxide film existing at a site different from the electrodes were scraped away, and a conductive paste (DOTITE D-550 manufactured by Fujikura Kasei Co., Ltd.) was attached thereto and a solvent was dried. Thus, a field effect transistor (FET) element having a top-contact bottom-gate structure was prepared.

Using the prepared coating FET element as a gate electrode, voltage was imparted to the silicon substrate. Electrical properties of the obtained deposition FET element were evaluated under vacuum ($<5 \times 10^{-3}$ Pa) by using a semiconductor device analyzer B1500A manufactured by Agilent Company.

As a result, the organic semiconductor element formed by using the compound exhibited properties as a pn-type transistor element. When carrier mobility was determined from a saturated region in current-voltage properties of the organic thin-film transistor, it exhibited $5.5 \times 10$ cm$^2$/V·s under vacuum.

While the present invention has been described in detail and with reference to specific embodiments thereof, it will be apparent to one skilled in the art that various changes and modifications can be made therein without departing from the spirit and scope thereof. The present application is based on Japanese Patent Application (No. 2012-033157) filed on Feb. 17, 2012, and the contents thereof are incorporated herein by reference.

INDUSTRIAL APPLICABILITY

The present invention provides a fluorine-containing aromatic compound applicable to both of a dry process and a wet process and expectable to have high carrier mobility.

By introducing a fluorine-containing alkyl group by using an acene that is a condensed aromatic ring compound as a core skeleton without using a metal coupling reaction, solubilization in an organic solvent and decrease in contamination with heavy metals are achieved, so that there can be obtained a fluorine-containing aromatic compound having high carrier mobility.

With the improvement in solubility in an organic solvent resulting from the substituent introduction and the improvement in the high carrier mobility resulting from the introduction of the fluorine-containing alkyl group, there is a very high possibility that an organic semiconductor material containing the compound is utilized in organic EL elements for next-generation flat panel displays, organic thin-film solar batteries as light-weight and flexible power sources, organic thin-film transistors, and the like.

The invention claimed is:
1. A method comprising:
reacting a compound represented by the following formula (1) with a compound represented by the formula R$_1$—Si(CH$_3$)$_3$ to obtain a compound represented by the following formula (1-1A);
deprotecting the compound represented by the formula (1-1A) to obtain a compound represented by the following formula (1-1B); and
aromatizing the compound represented by the formula (1-1B);
thereby obtaining a fluorine containing aromatic compound represented by the following formula (2-1):

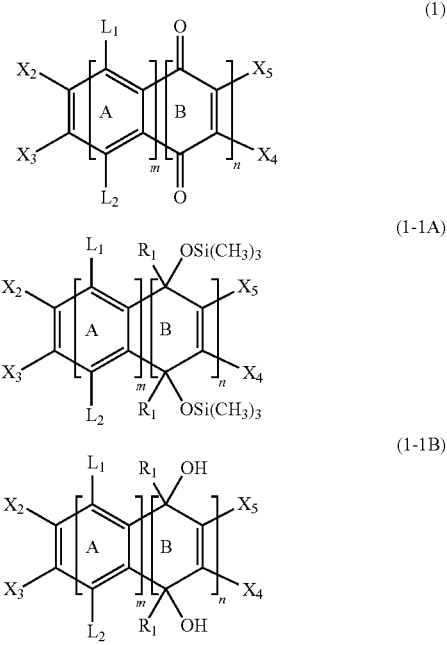

-continued (2-1)

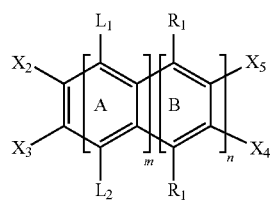

in the formulae, $R_1$ is a linear perfluoroalkyl group having a carbon number of 1 to 3;

$X_2$ to $X_5$ are a halogen atom or a hydrogen atom and they may be the same or different;

m and n are the numbers of repetitions of repeating unit structures A and B represented in parentheses, respectively, m is an integer of 0 or more, n is an integer of 1 or more, and m+n is an integer of 2 or more and 6 or less;

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different; in the case where m is 2 or more, a plurality of the $L_1$ groups present in the structure A may be the same or different and a plurality of the $L_2$ groups present in the structure A may be the same or different; and in the case where at least one of m and n is 2 or more, the order of combining the structure A and the structure B may be block or random.

2. The method according to claim 1, wherein a carbonate salt is added in the reacting step.

3. The method according to claim 1, wherein a triphenylphosphine and a carbon tetrabromide are used in the aromatizing step.

4. The method according to claim 1, wherein the compound represented by the formula (2-1) is a compound represented by the following formula (3-1):

(3-1)

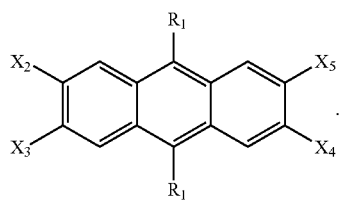

5. The method according to claim 1, wherein the compound represented by the formula (2-1) is a compound represented by the following formula (4-1) or a compound represented by the following formula (5-1):

(4-1)

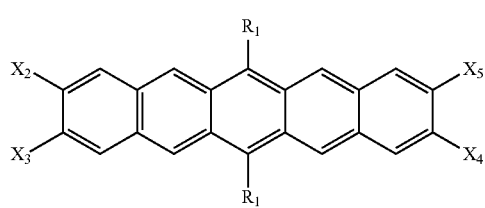

-continued (5-1)

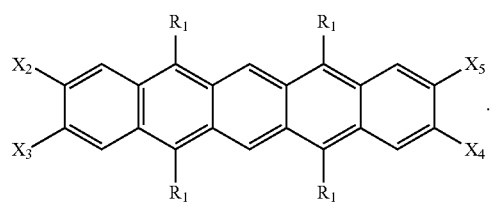

6. A method comprising:

replacing at least one of $X_2$ to $X_5$ as halogen atom(s), in a compound where at least one of $X_2$ to $X_5$ in a compound represented by the following formula (1) is a halogen atom, by a monovalent hydrocarbon group having a carbon number of 1 to 12 which may have a substituent, a monovalent aromatic hydrocarbon group which may have a substituent, or a monovalent heteroaromatic group which may have a substituent;

reacting the compound with a compound represented by the formula $R_1$—Si(CH$_3$)$_3$ to obtain a compound represented by the following formula (1-2A);

deprotecting the compound represented by the formula (1-2A) to obtain a compound represented by the following formula (1-2B); and aromatizing the compound represented by the formula (1-2B);

thereby obtaining a fluorine containing aromatic compound represented by the following formula (2-1):

(1)

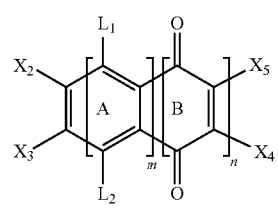

(1-2A)

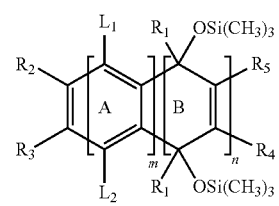

(1-2B)

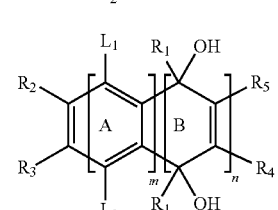

(2-2)

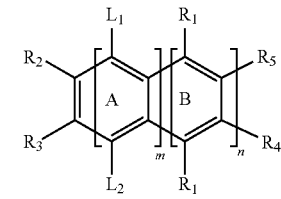

in the formulae, $R_1$ is a linear perfluoroalkyl group having a carbon number of 1 to 3;

$X_2$ to $X_5$ are a halogen atom or a hydrogen atom and they may be the same or different;

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom; one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent; and $R_2$ to $R_5$ may be the same or different;

m and n are the numbers of repetitions of repeating unit structures A and B represented in parentheses, respectively, m is an integer of 0 or more, n is an integer of 1 or more, and m+n is an integer of 2 or more and 6 or less;

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different; in the case where m is 2 or more, a plurality of the $L_1$ groups present in the structure A may be the same or different and a plurality of the $L_2$ groups present in the structure A may be the same or different; and in the case where at least one of m and n is 2 or more, the order of combining the structure A and the structure B may be block or random.

7. The method according to claim 6, wherein a carbonate salt is added in the reacting step.

8. The method according to claim 6, wherein a triphenylphosphine and a carbon tetrabromide are used in the aromatizing step.

9. The method according to claim 6, wherein the compound represented by the formula (2-2) is a compound represented by the following formula (3-2):

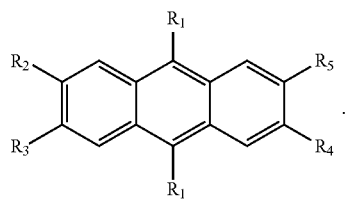

(3-2)

10. The method according to claim 6, wherein the compound represented by the formula (2-2) is a compound represented by the following formula (4-2) or a compound represented by the following formula (5-2):

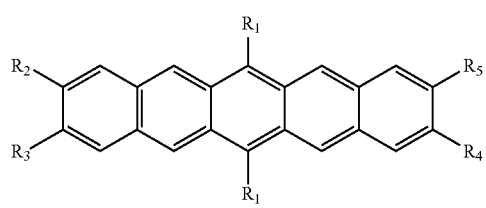

(4-2)

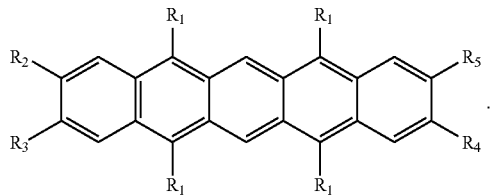

(5-2)

11. A method comprising:

replacing at least one halogen atom of a compound represented by the following formula (2-1) where at least one of $X_2$ to $X_5$ is a halogen atom by a monovalent hydrocarbon group having a carbon number of 1 to 12 which may have a substituent, a monovalent aromatic hydrocarbon group which may have a substituent, a monovalent heteroaromatic group which may have a substituent, and thereby obtaining a compound represented by the following formula (2-2):

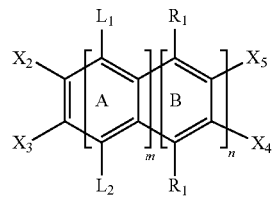

(2-1)

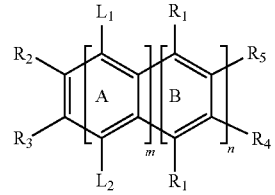

(2-2)

in the formulae, $R_1$ is a linear perfluoroalkyl group having a carbon number of 1 to 3;

$X_2$ to $X_5$ are a halogen atom or a hydrogen atom and they may be the same or different;

$R_2$ to $R_5$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom; one or more groups selected from $R_2$ to $R_5$ are a monovalent hydrocarbon group having a carbon number of 1 to 12 which may have a substituent, a monovalent aromatic hydrocarbon group which may have a substituent, or a monovalent heteroaromatic group which may have a substituent and $R_2$ to $R_5$ may be the same or different;

m and n are the numbers of repetitions of repeating unit structures A and B represented in parentheses, respectively, m is an integer of 0 or more, n is an integer of 1 or more, and m+n is an integer of 2 or more and 6 or less;

$L_1$ and $L_2$ are a monovalent hydrocarbon group having a carbon number of 1 to 12 which may have a substituent, a monovalent aromatic hydrocarbon group which may have a substituent, a monovalent heteroaromatic group which may have a substituent, a halogen atom, or a hydrogen atom, and they may be the same or different; in the case where m is 2 or more, a plurality of the $L_1$ groups present in the structure A may be the same or different and a plurality of the $L_2$ groups present in the structure A may be the same or different; and in the case where at least one of m and n is 2 or more, the order of combining the structure A and the structure B may be block or random.

12. The method according to claim 11, wherein the compound represented by the formula (2-1) is a compound represented by the following formula (3-1) and the compound represented by the formula (2-2) is a compound represented by the following formula (3-2):

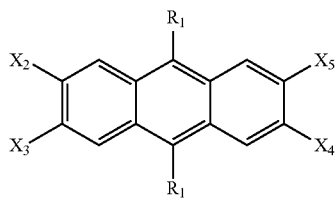

(3-1)

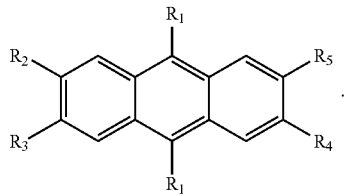

(3-2)

13. The method according to claim 11, wherein the compound represented by the formula (2-1) is a compound represented by the following formula (4-1) or a compound represented by the following formula (5-1) and the compound represented by the formula (2-2) is a compound represented by the following formula (4-2) or a compound represented by the following formula (5-2):

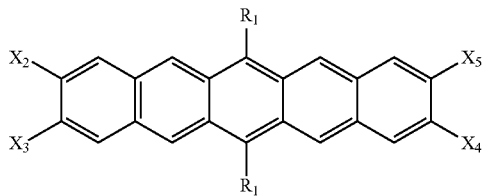

(4-1)

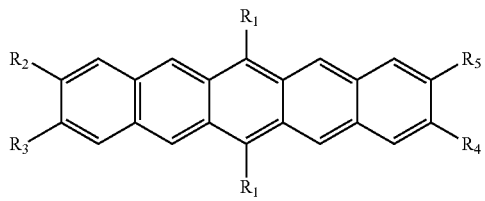

(4-2)

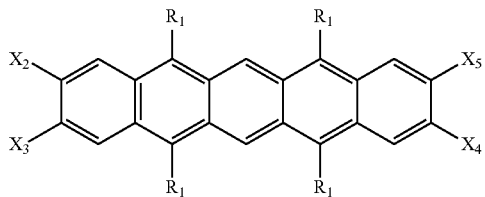

(5-1)

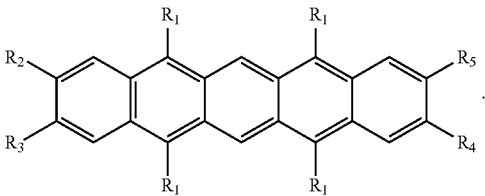

(5-2)

* * * * *